US012721596B2

(12) United States Patent
Tran

(10) Patent No.: US 12,721,596 B2
(45) **Date of Patent: *Sep. 1, 2026**

(54) ULTRASOUND PROBE WITH PRESSURE MEASUREMENT CAPABILITY

(71) Applicant: Bard Access Systems, Inc., Salt Lake City, UT (US)

(72) Inventor: Huy Ngoc Tran, Riverton, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/058,331

(22) Filed: Feb. 20, 2025

(65) Prior Publication Data

US 2025/0186026 A1 Jun. 12, 2025

Related U.S. Application Data

(63) Continuation of application No. 17/471,015, filed on Sep. 9, 2021, now Pat. No. 12,232,910.
(Continued)

(51) Int. Cl.
*A61B 8/00* (2006.01)
*A61B 8/08* (2006.01)

(52) U.S. Cl.
CPC .......... *A61B 8/4444* (2013.01); *A61B 8/0841* (2013.01); *A61B 8/085* (2013.01); *A61B 8/463* (2013.01)

(58) Field of Classification Search
CPC ..... A61B 8/4444; A61B 8/0841; A61B 8/085; A61B 8/463; A61B 8/4218; A61B 8/0891; A61B 8/4254
See application file for complete search history.

(56) References Cited

U.S. PATENT DOCUMENTS 3,697,917 A 10/1972 Orth et al.
5,148,809 A 9/1992 Biegeleisen-Knight et al.
(Continued)

FOREIGN PATENT DOCUMENTS

CN 102871645 A 1/2013
CN 105107067 B 5/2018
(Continued)

OTHER PUBLICATIONS

Konica Minolta, "Vascular NAVI" product website. https://www.konicaminolta.com/global-en/healthcare/technology/ultrasound/vascularnavi/index.html. Last accessed Jun. 2025.
(Continued)

*Primary Examiner* — Sanjay Cattungal
(74) *Attorney, Agent, or Firm* — Rutan & Tucker LLP

(57) ABSTRACT

Ultrasound probes, ultrasound systems, and ultrasound methods with pressure measurement capabilities for detecting and determining if bodily tissue is over-compressed during ultrasound imaging procedure. An ultrasound probe can include a probe body, an articulating probe head attached to the probe body, and a pressure-sensing device housed in an articulating area between the articulating probe head and the probe body. A method can include placing the articulating probe head of the ultrasound probe on a skin surface of a patient and moving the articulating probe head of the ultrasound probe over the patient while ultrasound signals are emitted into the patient from the articulating probe head. The method can also include monitoring for measured pressure values induced on the patient by the articulating probe head to determine whether a threshold pressure value has been exceeded.

9 Claims, 8 Drawing Sheets

Related U.S. Application Data

(60) Provisional application No. 63/076,589, filed on Sep. 10, 2020.

(56) References Cited

U.S. PATENT DOCUMENTS 5,181,513 A 1/1993 Touboul et al.
5,325,293 A 6/1994 Dorne
5,349,865 A 9/1994 Kavli et al.
5,441,052 A 8/1995 Miyajima
5,549,554 A 8/1996 Miraki
5,573,529 A 11/1996 Haak et al.
5,758,650 A 6/1998 Miller et al.
5,775,322 A 7/1998 Silverstein et al.
5,879,297 A 3/1999 Haynor et al.
5,897,503 A 4/1999 Lyon et al.
5,908,387 A 6/1999 LeFree et al.
5,967,984 A 10/1999 Chu et al.
5,970,119 A 10/1999 Hofmann
6,004,270 A 12/1999 Urbano et al.
6,019,724 A 2/2000 Gronningsaeter et al.
6,068,599 A 5/2000 Saito et al.
6,074,367 A 6/2000 Hubbell
6,129,668 A 10/2000 Haynor et al.
6,132,379 A 10/2000 Patacsil et al.
6,216,028 B1 4/2001 Haynor et al.
6,233,476 B1 5/2001 Strommer et al.
6,245,018 B1 6/2001 Lee
6,263,230 B1 7/2001 Haynor et al.
6,375,615 B1 4/2002 Flaherty et al.
6,436,043 B2 8/2002 Bonnefous
6,498,942 B1 12/2002 Esenaliev et al.
6,503,205 B2 1/2003 Manor et al.
6,508,769 B2 1/2003 Bonnefous
6,511,458 B2 1/2003 Milo et al.
6,524,249 B2 2/2003 Moehring et al.
6,543,642 B1 4/2003 Milliorn
6,554,771 B1 4/2003 Buil et al.
6,592,520 B1 7/2003 Peszynski et al.
6,592,565 B2 7/2003 Twardowski
6,601,705 B2 8/2003 Molina et al.
6,612,992 B1 9/2003 Hossack et al.
6,613,002 B1 9/2003 Clark et al.
6,623,431 B1 9/2003 Sakuma et al.
6,641,538 B2 11/2003 Nakaya et al.
6,647,135 B2 11/2003 Bonnefous
6,687,386 B1 2/2004 Ito et al.
6,733,458 B1 5/2004 Steins et al.
6,749,569 B1 6/2004 Pellegretti
6,754,608 B2 6/2004 Svanerudh et al.
6,755,789 B2 6/2004 Stringer et al.
6,840,379 B2 1/2005 Franks-Farah et al.
6,857,196 B2 2/2005 Dalrymple
6,979,294 B1 12/2005 Selzer et al.
7,074,187 B2 7/2006 Selzer et al.
7,244,234 B2 7/2007 Ridley et al.
7,359,554 B2 4/2008 Klingensmith et al.
7,534,209 B2 5/2009 Abend et al.
7,599,730 B2 10/2009 Hunter et al.
7,637,870 B2 12/2009 Flaherty et al.
7,681,579 B2 3/2010 Schwartz
7,691,061 B2 4/2010 Hirota
7,699,779 B2 4/2010 Sasaki et al.
7,720,520 B2 5/2010 Willis
7,727,153 B2 6/2010 Fritz et al.
7,734,326 B2 6/2010 Pedain et al.
7,831,449 B2 11/2010 Ying et al.
7,905,837 B2 3/2011 Suzuki
7,925,327 B2 4/2011 Weese
7,927,278 B2 4/2011 Selzer et al.
8,014,848 B2 9/2011 Birkenbach et al.
8,038,619 B2 10/2011 Steinbacher
8,060,181 B2 11/2011 Rodriguez Ponce et al.
8,075,488 B2 12/2011 Burton
8,090,427 B2 1/2012 Eck et al.
8,105,239 B2 1/2012 Specht
8,172,754 B2 5/2012 Watanabe et al.
8,175,368 B2 5/2012 Sathyanarayana
8,200,313 B1 6/2012 Rambod et al.
8,211,023 B2 7/2012 Swan et al.
8,228,347 B2 7/2012 Beasley et al.
8,298,147 B2 10/2012 Huennekens et al.
8,303,505 B2 11/2012 Webler et al.
8,323,202 B2 12/2012 Roschak et al.
8,328,727 B2 12/2012 Miele et al.
8,336,536 B1 12/2012 Wood-Putnam et al.
8,388,541 B2 3/2013 Messerly et al.
8,409,103 B2 4/2013 Grunwald et al.
8,449,465 B2 5/2013 Nair et al.
8,553,954 B2 10/2013 Saikia
8,556,815 B2 10/2013 Pelissier et al.
8,585,600 B2 11/2013 Liu et al.
8,622,913 B2 1/2014 Dentinger et al.
8,706,457 B2 4/2014 Hart et al.
8,727,988 B2 5/2014 Flaherty et al.
8,734,357 B2 5/2014 Taylor
8,744,211 B2 6/2014 Owen
8,754,865 B2 6/2014 Merritt et al.
8,764,663 B2 7/2014 Smok et al.
8,781,194 B2 7/2014 Malek et al.
8,781,555 B2 7/2014 Burnside et al.
8,790,263 B2 7/2014 Randall et al.
8,849,382 B2 9/2014 Cox et al.
8,939,908 B2 1/2015 Suzuki et al.
8,961,420 B2 2/2015 Zhang
9,022,940 B2 5/2015 Meier
9,087,147 B1 7/2015 Fonte
9,138,290 B2 9/2015 Hadjicostis
9,199,082 B1 12/2015 Yared et al.
9,204,858 B2 12/2015 Pelissier et al.
9,220,477 B2 12/2015 Urabe et al.
9,295,447 B2 3/2016 Shah
9,320,493 B2 4/2016 Visveshwara
9,357,980 B2 6/2016 Toji et al.
9,364,171 B2 6/2016 Harris et al.
9,427,207 B2 8/2016 Sheldon et al.
9,445,780 B2 9/2016 Hossack et al.
9,456,766 B2 10/2016 Cox et al.
9,456,804 B2 10/2016 Tamada
9,468,413 B2 10/2016 Hall et al.
9,492,097 B2 11/2016 Wilkes et al.
9,521,961 B2 12/2016 Silverstein et al.
9,554,716 B2 1/2017 Burnside et al.
9,582,876 B2 2/2017 Specht
9,610,061 B2 4/2017 Ebbini et al.
9,636,031 B2 5/2017 Cox
9,649,037 B2 5/2017 Lowe et al.
9,649,048 B2 5/2017 Cox et al.
9,702,969 B2 7/2017 Hope Simpson et al.
9,715,757 B2 7/2017 Ng et al.
9,717,415 B2 8/2017 Cohen et al.
9,731,066 B2 8/2017 Liu et al.
9,814,433 B2 11/2017 Benishti et al.
9,814,531 B2 11/2017 Yagi et al.
9,861,337 B2 1/2018 Patwardhan et al.
9,895,138 B2 2/2018 Sasaki
9,913,605 B2 3/2018 Harris et al.
9,949,720 B2 4/2018 Southard et al.
10,043,272 B2 8/2018 Forzoni et al.
10,449,330 B2 10/2019 Newman et al.
10,524,691 B2 1/2020 Newman et al.
10,751,509 B2 8/2020 Misener
11,564,861 B1 1/2023 Gaines
11,844,656 B2 12/2023 Urabe et al.
11,900,593 B2 2/2024 Dhatt et al.
12,082,976 B2 9/2024 Urabe et al.
2002/0038088 A1 3/2002 Imran et al.
2003/0047126 A1 3/2003 Tomaschko
2003/0106825 A1 6/2003 Molina et al.
2003/0109910 A1 6/2003 Lachenbruch et al.
2003/0120154 A1 6/2003 Sauer et al.
2003/0125629 A1 7/2003 Ustuner
2003/0135115 A1 7/2003 Burdette et al.
2003/0149366 A1 8/2003 Stringer et al.
2003/0167030 A1 9/2003 Weitzel et al.

(56) References Cited

U.S. PATENT DOCUMENTS

2003/0216648 A1 11/2003 Lizzi et al.
2004/0015080 A1 1/2004 Kelly et al.
2004/0055925 A1 3/2004 Franks-Farah et al.
2004/0197267 A1 10/2004 Black et al.
2005/0000975 A1 1/2005 Carco et al.
2005/0049504 A1 3/2005 Lo et al.
2005/0075597 A1 4/2005 Vournakis et al.
2005/0165299 A1 7/2005 Kressy et al.
2005/0251030 A1 11/2005 Azar et al.
2005/0267365 A1 12/2005 Sokulin et al.
2006/0004290 A1 1/2006 Smith et al.
2006/0013523 A1 1/2006 Childlers et al.
2006/0015039 A1 1/2006 Cassidy et al.
2006/0020204 A1 1/2006 Serra et al.
2006/0047617 A1 3/2006 Bacioiu et al.
2006/0079781 A1 4/2006 Germond-Rouet et al.
2006/0184029 A1 8/2006 Haim et al.
2006/0210130 A1 9/2006 Germond-Rouet et al.
2006/0241463 A1 10/2006 Shau et al.
2007/0043341 A1 2/2007 Anderson et al.
2007/0049822 A1 3/2007 Bunce et al.
2007/0073155 A1 3/2007 Park et al.
2007/0167738 A1 7/2007 Timinger et al.
2007/0199848 A1 8/2007 Ellswood et al.
2007/0239005 A1 10/2007 Ogasawara
2007/0239120 A1 10/2007 Brock et al.
2007/0249911 A1 10/2007 Simon
2007/0287886 A1 12/2007 Saadat
2008/0021322 A1 1/2008 Stone et al.
2008/0033293 A1 2/2008 Beasley et al.
2008/0033759 A1 2/2008 Finlay
2008/0051657 A1 2/2008 Rold
2008/0108930 A1 5/2008 Weitzel et al.
2008/0125651 A1 5/2008 Watanabe et al.
2008/0146915 A1 6/2008 McMorrow
2008/0177186 A1 7/2008 Slater et al.
2008/0221425 A1 9/2008 Olson et al.
2008/0269605 A1 10/2008 Nakaya
2008/0294037 A1 11/2008 Richter
2008/0300491 A1 12/2008 Bonde et al.
2009/0012399 A1 1/2009 Sunagawa et al.
2009/0012401 A1 1/2009 Steinbacher
2009/0074280 A1 3/2009 Lu et al.
2009/0105594 A1 4/2009 Reynolds et al.
2009/0118612 A1 5/2009 Grunwald et al.
2009/0124903 A1 5/2009 Osaka
2009/0137887 A1 5/2009 Shariati et al.
2009/0137907 A1 5/2009 Takimoto et al.
2009/0143672 A1 6/2009 Harms et al.
2009/0143684 A1 6/2009 Cermak et al.
2009/0156926 A1 6/2009 Messerly et al.
2009/0171205 A1 7/2009 Kharin et al.
2009/0281413 A1 11/2009 Boyden et al.
2009/0306509 A1 12/2009 Pedersen et al.
2010/0010348 A1 1/2010 Halmann
2010/0168576 A1 7/2010 Poland et al.
2010/0211026 A2 8/2010 Sheetz et al.
2010/0249598 A1 9/2010 Smith et al.
2010/0286515 A1 11/2010 Gravenstein et al.
2010/0298705 A1 11/2010 Pelissier et al.
2010/0312121 A1 12/2010 Guan
2010/0324423 A1 12/2010 El-Aklouk et al.
2011/0002518 A1 1/2011 Ziv-Ari et al.
2011/0026796 A1 2/2011 Hyun et al.
2011/0071404 A1 3/2011 Schmitt et al.
2011/0074244 A1 3/2011 Osawa
2011/0087107 A1 4/2011 Lindekugel et al.
2011/0137173 A1 6/2011 Lowe et al.
2011/0166451 A1 7/2011 Blaivas et al.
2011/0282188 A1 11/2011 Burnside et al.
2011/0295108 A1 12/2011 Cox et al.
2011/0313293 A1 12/2011 Lindekugel et al.
2012/0136242 A1 5/2012 Qi et al.
2012/0136256 A1 5/2012 Nozaki et al.
2012/0143029 A1 6/2012 Silverstein et al.
2012/0165679 A1 6/2012 Orome et al.
2012/0179038 A1 7/2012 Meurer et al.
2012/0179042 A1 7/2012 Fukumoto et al.
2012/0179044 A1 7/2012 Chiang et al.
2012/0197132 A1 8/2012 O'Connor
2012/0220865 A1 8/2012 Brown et al.
2012/0277576 A1 11/2012 Lui
2013/0041250 A1 2/2013 Pelissier et al.
2013/0102889 A1 4/2013 Southard et al.
2013/0131499 A1 5/2013 Chan et al.
2013/0131502 A1 5/2013 Blaivas et al.
2013/0144166 A1 6/2013 Specht et al.
2013/0150724 A1 6/2013 Blaivas et al.
2013/0188832 A1 7/2013 Ma et al.
2013/0197367 A1 8/2013 Smok et al.
2013/0218024 A1 8/2013 Boctor et al.
2013/0323700 A1 12/2013 Samosky et al.
2013/0338503 A1 12/2013 Cohen et al.
2013/0338508 A1 12/2013 Nakamura et al.
2013/0345566 A1 12/2013 Weitzel et al.
2014/0005530 A1 1/2014 Liu et al.
2014/0031694 A1 1/2014 Solek
2014/0066779 A1 3/2014 Nakanishi
2014/0073976 A1 3/2014 Fonte et al.
2014/0100440 A1 4/2014 Cheline et al.
2014/0114194 A1 4/2014 Kanayama et al.
2014/0170620 A1 6/2014 Savitsky et al.
2014/0180098 A1 6/2014 Flaherty et al.
2014/0180116 A1 6/2014 Lindekugel et al.
2014/0188133 A1 7/2014 Misener
2014/0188440 A1 7/2014 Donhowe et al.
2014/0276048 A1 9/2014 Kiley et al.
2014/0276059 A1 9/2014 Sheehan
2014/0276069 A1 9/2014 Amble et al.
2014/0276081 A1 9/2014 Tegels
2014/0276085 A1 9/2014 Miller
2014/0276690 A1 9/2014 Grace
2014/0296694 A1 10/2014 Jaworski
2014/0343431 A1 11/2014 Vajinepalli et al.
2014/0357994 A1 12/2014 Jin et al.
2015/0005738 A1 1/2015 Blacker
2015/0011887 A1 1/2015 Ahn et al.
2015/0065916 A1 3/2015 Maguire et al.
2015/0073279 A1 3/2015 Cai et al.
2015/0080740 A1 3/2015 Hao et al.
2015/0112200 A1 4/2015 Oberg et al.
2015/0141821 A1 5/2015 Yoshikawa et al.
2015/0190111 A1 7/2015 Fry
2015/0209003 A1 7/2015 Halmann et al.
2015/0209113 A1 7/2015 Burkholz et al.
2015/0209510 A1 7/2015 Burkholz et al.
2015/0209526 A1 7/2015 Matsubara et al.
2015/0245820 A1 9/2015 Tamada
2015/0257735 A1 9/2015 Ball et al.
2015/0272448 A1 10/2015 Fonte et al.
2015/0282890 A1 10/2015 Cohen et al.
2015/0294497 A1 10/2015 Ng et al.
2015/0297097 A1 10/2015 Matsubara et al.
2015/0342572 A1 12/2015 Tahmasebi Maraghoosh et al.
2015/0359520 A1 12/2015 Shan et al.
2015/0359991 A1 12/2015 Dunbar et al.
2016/0000367 A1 1/2016 Lyon
2016/0000399 A1 1/2016 Halmann et al.
2016/0026894 A1 1/2016 Nagase
2016/0029995 A1 2/2016 Navratil et al.
2016/0038119 A1 2/2016 Desjardins
2016/0081674 A1 3/2016 Bagwan et al.
2016/0113517 A1 4/2016 Lee et al.
2016/0113699 A1 4/2016 Sverdlik et al.
2016/0120607 A1 5/2016 Sorotzkin et al.
2016/0125639 A1 5/2016 Park et al.
2016/0157831 A1 6/2016 Kang et al.
2016/0166232 A1 6/2016 Merritt
2016/0202053 A1 7/2016 Walker et al.
2016/0211045 A1 7/2016 Jeon et al.
2016/0213398 A1 7/2016 Liu
2016/0220124 A1 8/2016 Grady et al.
2016/0259992 A1 9/2016 Knodt et al.
2016/0278869 A1 9/2016 Grunwald

(56) References Cited

U.S. PATENT DOCUMENTS

2016/0287214 A1 10/2016 Ralovich et al.
2016/0296208 A1 10/2016 Sethuraman et al.
2016/0374644 A1 12/2016 Mauldin, Jr. et al.
2017/0014105 A1 1/2017 Chono
2017/0020561 A1 1/2017 Cox et al.
2017/0079548 A1 3/2017 Silverstein et al.
2017/0086785 A1 3/2017 Bjaerum
2017/0090571 A1 3/2017 Bjaerum et al.
2017/0103534 A1 4/2017 Park et al.
2017/0143312 A1 5/2017 Hedlund et al.
2017/0157339 A1 6/2017 Li et al.
2017/0164923 A1 6/2017 Matsumoto
2017/0172666 A1 6/2017 Govari et al.
2017/0215842 A1 8/2017 Ryu et al.
2017/0231553 A1 8/2017 Igarashi et al.
2017/0252004 A1 9/2017 Broad et al.
2017/0258522 A1 9/2017 Goshgarian et al.
2017/0259013 A1 9/2017 Boyden et al.
2017/0262982 A1 9/2017 Pagoulatos et al.
2017/0328751 A1 11/2017 Lemke
2017/0367678 A1 12/2017 Sirtori et al.
2018/0015256 A1 1/2018 Southard et al.
2018/0028110 A1 2/2018 Goldman et al.
2018/0116723 A1 5/2018 Hettrick et al.
2018/0125450 A1 5/2018 Blackbourne et al.
2018/0161502 A1 6/2018 Nanan et al.
2018/0199914 A1 7/2018 Ramachandran et al.
2018/0214119 A1 8/2018 Mehrmohammadi et al.
2018/0228465 A1 8/2018 Southard et al.
2018/0235649 A1 8/2018 Elkadi
2018/0235709 A1 8/2018 Donhowe et al.
2018/0289927 A1 10/2018 Messerly
2018/0296185 A1 10/2018 Cox et al.
2018/0310955 A1 11/2018 Lindekugel et al.
2018/0333135 A1 11/2018 Kim et al.
2018/0344293 A1 12/2018 Raju et al.
2019/0029636 A1 1/2019 Lee et al.
2019/0060001 A1 2/2019 Kohli et al.
2019/0060014 A1 2/2019 Hazelton et al.
2019/0090855 A1 3/2019 Kobayashi et al.
2019/0125210 A1 5/2019 Govari et al.
2019/0200951 A1 7/2019 Meier
2019/0239848 A1 8/2019 Bedi et al.
2019/0239850 A1 8/2019 Dalvin et al.
2019/0307419 A1 10/2019 Durfee
2019/0307515 A1 10/2019 Naito et al.
2019/0307516 A1 10/2019 Schotzko et al.
2019/0365347 A1 12/2019 Abe
2019/0365348 A1 12/2019 Toume et al.
2019/0365354 A1 12/2019 Du
2019/0380676 A1 12/2019 Swan et al.
2020/0027210 A1 1/2020 Haemel et al.
2020/0069929 A1 3/2020 Mason et al.
2020/0085381 A1 3/2020 Weine et al.
2020/0107596 A1 4/2020 Caruso et al.
2020/0113540 A1 4/2020 Gijsbers et al.
2020/0163654 A1 5/2020 Satir et al.
2020/0200900 A1 6/2020 Asami et al.
2020/0229795 A1 7/2020 Tadross et al.
2020/0230391 A1 7/2020 Burkholz et al.
2020/0237403 A1 7/2020 Southard et al.
2020/0238403 A1 7/2020 Ahn et al.
2020/0281563 A1 9/2020 Muller et al.
2020/0359990 A1 11/2020 Poland et al.
2020/0390416 A1 12/2020 Swan et al.
2021/0045716 A1 2/2021 Shiran et al.
2021/0059639 A1 3/2021 Howell
2021/0077058 A1 3/2021 Mashood et al.
2021/0093383 A1 4/2021 Wang et al.
2021/0137492 A1 5/2021 Imai
2021/0146167 A1 5/2021 Barthe et al.
2021/0161510 A1 6/2021 Sasaki et al.
2021/0186467 A1 6/2021 Urabe et al.
2021/0212658 A1 7/2021 McGrath et al.
2021/0212668 A1 7/2021 Li et al.
2021/0267569 A1 9/2021 Yamamoto
2021/0267570 A1 9/2021 Ulman et al.
2021/0295048 A1 9/2021 Buras et al.
2021/0315538 A1 10/2021 Brandl et al.
2021/0373602 A1 12/2021 Min
2021/0378627 A1 12/2021 Yarmush et al.
2022/0019313 A1 1/2022 He et al.
2022/0022969 A1 1/2022 Misener
2022/0039777 A1 2/2022 Durfee
2022/0039829 A1 2/2022 Zijlstra et al.
2022/0071593 A1 3/2022 Tran
2022/0096053 A1 3/2022 Sethuraman et al.
2022/0096797 A1 3/2022 Prince
2022/0101980 A1 3/2022 Rothenberg et al.
2022/0104791 A1 4/2022 Matsumoto
2022/0104886 A1 4/2022 Blanchard et al.
2022/0117582 A1 4/2022 McLaughlin et al.
2022/0160434 A1 5/2022 Messerly et al.
2022/0168050 A1 6/2022 Sowards et al.
2022/0172354 A1 6/2022 Misener et al.
2022/0225963 A1 7/2022 Sutton et al.
2022/0233346 A1 7/2022 McElya
2022/0296303 A1 9/2022 McLeod et al.
2022/0304652 A1 9/2022 Peterson et al.
2022/0330922 A1 10/2022 Sowards et al.
2022/0334251 A1 10/2022 Sowards et al.
2022/0338833 A1 10/2022 Dhatt et al.
2022/0361840 A1 11/2022 Matsumoto et al.
2022/0406460 A1 12/2022 Golan et al.
2023/0044620 A1 2/2023 Shochat et al.
2023/0048327 A1 2/2023 Lampe et al.
2023/0107629 A1 4/2023 Sowards et al.
2023/0113291 A1 4/2023 de Wild et al.
2023/0132148 A1 4/2023 Sowards et al.
2023/0135562 A1 5/2023 Misener et al.
2023/0135757 A1 5/2023 Bauer et al.
2023/0138970 A1 5/2023 Sowards et al.
2023/0148872 A1 5/2023 Sowards et al.
2023/0201539 A1 6/2023 Howell
2023/0277153 A1 9/2023 Sowards et al.
2023/0277154 A1 9/2023 Sowards et al.
2023/0293143 A1 9/2023 Sowards et al.
2023/0298757 A1 9/2023 Golan et al.
2023/0338010 A1 10/2023 Sturm
2023/0371928 A1 11/2023 Rajguru et al.
2023/0381472 A1 11/2023 Chisena et al.
2023/0397900 A1 12/2023 Prince
2024/0065673 A1 2/2024 Sowards et al.
2024/0197403 A1 6/2024 Mino et al.
2024/0307024 A1 9/2024 Sowards et al.
2025/0017559 A1 1/2025 Denny et al.
2025/0057501 A1 2/2025 Prince
2025/0104238 A1 3/2025 Misener et al.
2025/0177060 A1 6/2025 Messerly et al.
2025/0251511 A1 8/2025 Sowards et al.
2025/0352167 A1 11/2025 Sowards et al.
2026/0123906 A1 5/2026 Sowards et al.

FOREIGN PATENT DOCUMENTS

EP 0933063 A1 8/1999
EP 1504713 A1 2/2005
EP 1591074 B1 5/2008
EP 2823766 A1 1/2015
EP 3181083 A1 6/2017
EP 3870059 9/2021
JP 2000271136 A 10/2000
JP 2007222291 A 9/2007
JP 2014150928 A 8/2014
JP 2018175547 A 11/2018
KR 20180070878 A 6/2018
KR 102176196 B1 11/2020
WO 2004082749 A2 9/2004
WO 2007115174 A2 10/2007
WO 2010029521 A2 3/2010
WO 2010076808 A1 7/2010
WO 2013059714 A1 4/2013
WO 2014115150 A1 7/2014
WO 2015017270 A1 2/2015

(56) References Cited

FOREIGN PATENT DOCUMENTS

| | | | |
|---|---|---|---|
| WO | 2016081023 | A1 | 5/2016 |
| WO | 2017096487 | A1 | 6/2017 |
| WO | 2017214428 | A1 | 12/2017 |
| WO | 2018026878 | A1 | 2/2018 |
| WO | 2018134726 | A1 | 7/2018 |
| WO | 2018138343 | A1 | 8/2018 |
| WO | 2019232451 | A1 | 12/2019 |
| WO | 2020002620 | A1 | 1/2020 |
| WO | 2020016018 | A1 | 1/2020 |
| WO | 2019232454 | A9 | 2/2020 |
| WO | 2020044769 | A1 | 3/2020 |
| WO | 2020067897 | A1 | 4/2020 |
| WO | 2020083660 | A1 | 4/2020 |
| WO | 2020186198 | A1 | 9/2020 |
| WO | 2021123905 | A2 | 6/2021 |
| WO | 2021198226 | A1 | 10/2021 |
| WO | 2022069208 | A1 | 4/2022 |
| WO | 2022072727 | A2 | 4/2022 |
| WO | 2022081904 | A1 | 4/2022 |
| WO | 2022115479 | A1 | 6/2022 |
| WO | 2022119853 | A1 | 6/2022 |
| WO | 2022119856 | A1 | 6/2022 |
| WO | 2022221703 | A1 | 10/2022 |
| WO | 2022221714 | A1 | 10/2022 |
| WO | 2023059512 | A1 | 4/2023 |
| WO | 2023076268 | A1 | 5/2023 |
| WO | 2023081220 | A1 | 5/2023 |
| WO | 2023081223 | A1 | 5/2023 |
| WO | 2023091424 | A1 | 5/2023 |
| WO | 2023167866 | A1 | 9/2023 |
| WO | 2023177718 | A1 | 9/2023 |
| WO | 2024044277 | A1 | 2/2024 |
| WO | 2024180503 | A1 | 9/2024 |
| WO | 2025015198 | A1 | 1/2025 |

OTHER PUBLICATIONS

U.S. Appl. No. 17/684,180, filed Mar. 1, 2022 Advisory Action dated Aug. 22, 2025.
U.S. Appl. No. 17/684,180, filed Mar. 1, 2022 Notice of Allowance dated Sep. 30, 2025.
U.S. Appl. No. 17/722,151, filed Apr. 15, 2022 Final Office Action dated Jul. 11, 2025.
U.S. Appl. No. 17/894,460, filed Aug. 24, 2022 Examiner's Answer dated Oct. 2, 2025.
U.S. Appl. No. 17/987,698, filed Nov. 15, 2022 Final Office Action dated Sep. 12, 2025.
U.S. Appl. No. 18/113,003, filed Feb. 22, 2023 Notice of Allowance dated Aug. 15, 2025.
U.S. Appl. No. 18/221,318, filed Jul. 12, 2023 Final Office Action dated Oct. 14, 2025.
U.S. Appl. No. 17/722,151, filed Apr. 15, 2022 Advisory Action dated Oct. 16, 2025.
U.S. Appl. No. 17/722,151, filed Apr. 15, 2022 Non-Final Office Action dated Dec. 23, 2025.
U.S. Appl. No. 17/894,460, filed Aug. 24, 2022 Non-Final Office Action dated Jan. 14, 2026.
U.S. Appl. No. 17/973,171, filed Oct. 25, 2022 Examiner's Answer dated Jan. 28, 2026.
U.S. Appl. No. 17/987,698, filed Nov. 15, 2022 Advisory Action dated Nov. 21, 2025.
U.S. Appl. No. 18/936,351, filed Nov. 4, 2024 Non-Final Office Action dated Nov. 10, 2025.
U.S. Appl. No. 17/538,911, filed Nov. 30, 2021 Final Office Action dated Sep. 13, 2023.
U.S. Appl. No. 17/538,911, filed Nov. 30, 2021 Non-Final Office Action dated Mar. 2, 2023.
U.S. Appl. No. 17/538,911, filed Nov. 30, 2021 Notice of Allowance dated Mar. 14, 2024.
U.S. Appl. No. 17/538,943, filed Nov. 30, 2021 Non-Final Office Action dated Jan. 30, 2024.
U.S. Appl. No. 17/538,943, filed Nov. 30, 2021 Notice of Allowance dated Aug. 14, 2024.
U.S. Appl. No. 17/684,180, filed Mar. 1, 2022 Advisory Action dated Apr. 4, 2024.
U.S. Appl. No. 17/684,180, filed Mar. 1, 2022 Advisory Action dated Dec. 27, 2024.
U.S. Appl. No. 17/684,180, filed Mar. 1, 2022 Final Office Action dated Jan. 18, 2024.
U.S. Appl. No. 17/684,180, filed Mar. 1, 2022 Final Office Action dated Sep. 23, 2024.
U.S. Appl. No. 17/684,180, filed Mar. 1, 2022 Non-Final Office Action dated Jan. 17, 2025.
U.S. Appl. No. 17/684,180, filed Mar. 1, 2022 Non-Final Office Action dated Jul. 28, 2023.
U.S. Appl. No. 17/684,180, filed Mar. 1, 2022 Non-Final Office Action dated May 8, 2024.
U.S. Appl. No. 17/684,180, filed Mar. 1, 2022 Restriction Requirement dated May 19, 2023.
U.S. Appl. No. 17/722,111, filed Apr. 15, 2022 Advisory Action dated Oct. 23, 2024.
U.S. Appl. No. 17/722,111, filed Apr. 15, 2022 Final Office Action dated Jul. 12, 2024.
U.S. Appl. No. 17/722,111, filed Apr. 15, 2022 Non-Final Office Action dated Dec. 22, 2023.
U.S. Appl. No. 17/722,111, filed Apr. 15, 2022 Notice of Allowance dated Dec. 18, 2024.
U.S. Appl. No. 17/722,151, filed Apr. 15, 2022 Advisory Action dated Dec. 27, 2024.
U.S. Appl. No. 17/722,151, filed Apr. 15, 2022 Advisory Action dated Jan. 2, 2024.
U.S. Appl. No. 17/722,151, filed Apr. 15, 2022 Final Office Action dated Nov. 6, 2023.
U.S. Appl. No. 17/722,151, filed Apr. 15, 2022 Final Office Action dated Sep. 20, 2024.
U.S. Appl. No. 17/722,151, filed Apr. 15, 2022 Non-Final Office Action dated Mar. 21, 2025.
U.S. Appl. No. 17/722,151, filed Apr. 15, 2022 Non-Final Office Action dated Mar. 25, 2024.
U.S. Appl. No. 17/722,151, filed Apr. 15, 2022 Non-Final Office Action dated Sep. 7, 2023.
U.S. Appl. No. 17/894,460, filed Aug. 24, 2022 Advisory Action dated Apr. 4, 2024.
U.S. Appl. No. 17/894,460, filed Aug. 24, 2022 Advisory Action dated Mar. 13, 2025.
U.S. Appl. No. 17/894,460, filed Aug. 24, 2022 Final Office Action dated Dec. 31, 2024.
U.S. Appl. No. 17/894,460, filed Aug. 24, 2022 Final Office Action dated Jan. 31, 2024.
U.S. Appl. No. 17/894,460, filed Aug. 24, 2022 Non-Final Office Action dated Nov. 6, 2023.
U.S. Appl. No. 17/894,460, filed Aug. 24, 2022 Non-Final Office Action dated Sep. 25, 2024.
U.S. Appl. No. 17/957,562, filed Sep. 30, 2022 Advisory Action dated Feb. 12, 2025.
U.S. Appl. No. 17/957,562, filed Sep. 30, 2022 Final Office Action dated Nov. 27, 2024.
U.S. Appl. No. 17/957,562, filed Sep. 30, 2022 Non-Final Office Action dated Jun. 20, 2024.
U.S. Appl. No. 17/973,171, filed Oct. 25, 2022 Non-Final Office Action dated Dec. 6, 2024.
U.S. Appl. No. 17/979,564, filed Nov. 2, 2022 Advisory Action dated Jan. 17, 2025.
U.S. Appl. No. 17/979,564, filed Nov. 2, 2022 Final Office Action dated Oct. 18, 2024.
U.S. Appl. No. 17/979,564, filed Nov. 2, 2022 Non-Final Office Action dated Jun. 5, 2024.
U.S. Appl. No. 17/979,601, filed Nov. 2, 2022 Advisory Action dated Feb. 11, 2025.
U.S. Appl. No. 17/979,601, filed Nov. 2, 2022 Final Office Action dated Dec. 5, 2024.
U.S. Appl. No. 17/979,601, filed Nov. 2, 2022 Non-Final Office Action dated Aug. 20, 2024.

(56) References Cited

OTHER PUBLICATIONS

U.S. Appl. No. 17/987,698, filed Nov. 15, 2022 Advisory Action dated Feb. 21, 2025.
U.S. Appl. No. 17/987,698, filed Nov. 15, 2022 Final Office Action dated Dec. 13, 2024.
U.S. Appl. No. 17/987,698, filed Nov. 15, 2022 Non-Final Office Action dated Sep. 20, 2024.
U.S. Appl. No. 18/113,003, filed Feb. 22, 2023 Non-Final Office Action dated Nov. 27, 2024.
U.S. Appl. No. 18/121,802, filed Mar. 15, 2023 Non-Final Office Action dated Dec. 16, 2024.
U.S. Appl. No. 18/238,281, filed Aug. 25, 2023 Non-Final Office Action dated Mar. 22, 2024.
U.S. Appl. No. 18/238,281, filed Aug. 25, 2023 Notice of Allowance dated Jul. 16, 2024.
U.S. Appl. No. 18/674,601, filed May 24, 2024 Non-Final Office Action dated Jan. 7, 2025.
William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
Chen et al.,3D near infrared and ultrasound imaging of peripheral blood vessels for real-time localization and needle guidance. InMedical Image Computing and Computer-Assisted Intervention-MICCAI 2016 (pp. 388-396) (Year: 2016).
U.S. Appl. No. 17/684,180, filed Mar. 1, 2022 Final Office Action dated May 29, 2025.
U.S. Appl. No. 17/957,562, filed Sep. 30, 2022 Examiner's Answer dated Jun. 16, 2025.
U.S. Appl. No. 17/973,171, filed Oct. 25, 2022 Advisory Action dated Jun. 30, 2025.
U.S. Appl. No. 17/973,171, filed Oct. 25, 2022 Final Office Action dated Apr. 3, 2025.
U.S. Appl. No. 17/979,564, filed Nov. 2, 2022 Examiner's Answer dated May 30, 2025.
U.S. Appl. No. 17/979,601, filed Nov. 2, 2022 Notice of Allowance dated Mar. 27, 2025.
U.S. Appl. No. 17/987,698, filed Nov. 15, 2022 Non-Final Office Action dated May 23, 2025.
U.S. Appl. No. 18/113,003, filed Feb. 22, 2023 Advisory Action dated Jul. 2, 2025.
U.S. Appl. No. 18/113,003, filed Feb. 22, 2023 Final Office Action dated Apr. 29, 2025.
U.S. Appl. No. 18/121,802, filed Mar. 15, 2023 Notice of Allowance dated Jun. 5, 2025.
U.S. Appl. No. 18/221,318, filed Jul. 12, 2023 Non-Final Office Action dated Jun. 23, 2025.
U.S. Appl. No. 18/221,318, filed Jul. 12, 2023 Restriction Requirement dated Mar. 28, 2025.
U.S. Appl. No. 18/674,601, filed May 24, 2024 Notice of Allowance dated Mar. 26, 2025.
EP 20866520.8 filed Apr. 5, 2022 Extended European Search Report dated Aug. 22, 2023.
Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).
M. Ikhsan, K. K. Tan, AS. Putra, C. F. Kong, et al., "Automatic identification of blood vessel cross-section for central venous catheter placement using a cascading classifier," 39th Annual International Conference of the IEEE Engineering in Medicine and Biology Society (EMBC).pp. 1489-1492 (Year: 2017).
Pagoulatos, N. et al. "New spatial localizer based on fiber optics with applications in 3D ultrasound imaging" Proceeding of Spie, vol. 3976 (Apr. 18, 2000; Apr. 18, 2000).
PCT/US2021/049294 filed Sep. 7, 2021 International Search Report and Written Opinion dated Dec. 8, 2021.
PCT/US2021/049712 filed Sep. 9, 2021 International Search Report and Written Opinion dated Dec. 14, 2021.
PCT/US2021/060622 filed Nov. 23, 2021 International Search Report and Written Opinion dated Mar. 3, 2022.
PCT/US2021/061267 filed Nov. 30, 2021 International Search Report and Written Opinion dated Mar. 9, 2022.
PCT/US2021/061276 filed Nov. 30, 2021 International Search Report and Written Opinion dated Mar. 9, 2022.
PCT/US2022/025082 filed Apr. 15, 2022 International Search Report and Written Opinion dated Jul. 11, 2022.
PCT/US2022/025097 filed Apr. 15, 2021 International Preliminary Report on Patentability dated Oct. 26, 2023.
PCT/US2022/025097 filed Apr. 15, 2022 International Search Report and Written Opinion dated Jul. 8, 2022.
PCT/US2022/045372 filed Sep. 30, 2022 International Search Report and Written Opinion dated Jan. 14, 2023.
PCT/US2022/048716 filed Nov. 2, 2022 International Search Report and Written Opinion dated Feb. 24, 2023.
PCT/US2022/048722 filed Nov. 2, 2022 International Search Report and Written Opinion dated Feb. 24, 2023.
PCT/US2022/049983 filed Nov. 15, 2022 International Search Report and Written Opinion dated Mar. 29, 2023.
PCT/US2022047727 filed Oct. 25, 2022 International Search Report and Written Opinion dated Jan. 25, 2023.
PCT/US2023/014143 filed Feb. 28, 2023 International Search Report and Written Opinion dated Jun. 12, 2023.
PCT/US2023/015266 filed Mar. 15, 2023 International Search Report and Written Opinion dated May 25, 2023.
PCT/US2023/030970 filed Aug. 23, 2023 International Search Report and Written Opinion dated Oct. 30, 2023.
PCT/US2024/037647 filed Jul. 11, 2024 International Search Report and Written Opinion dated Oct. 16, 2024.
Saxena Ashish et al Thermographic venous blood flow characterization with external cooling stimulation Infrared Physics and Technology Elsevier Science GB vol. 90 Feb. 9, 2018 Feb. 9, 2018 pp. 8-19 XP085378852.
Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docld/1235/file/SebastianVogtDissertation.pdf.
Thermographic venous blood flow characterization with external cooling stimulation (Year: 2018).
U.S. Appl. No. 15/650,474, filed Jul. 14, 2017 Final Office Action dated Jun. 2, 2020.
U.S. Appl. No. 15/650,474, filed Jul. 14, 2017 Non-Final Office Action dated Dec. 16, 2019.
U.S. Appl. No. 15/650,474, filed Jul. 14, 2017 Notice of Allowance dated Dec. 11, 2020.
U.S. Appl. No. 15/650,474, filed Jul. 14, 2017 Notice of Allowance dated Mar. 1, 2021.
U.S. Appl. No. 17/020,476, filed Sep. 14, 2020 Advisory Action dated Aug. 19, 2022.
U.S. Appl. No. 17/020,476, filed Sep. 14, 2020 Final Office Action dated Jan. 5, 2023.
U.S. Appl. No. 17/020,476, filed Sep. 14, 2020 Final Office Action dated Jun. 9, 2022.
U.S. Appl. No. 17/020,476, filed Sep. 14, 2020 Non-Final Office Action dated Feb. 9, 2022.
U.S. Appl. No. 17/020,476, filed Sep. 14, 2020 Non-Final Office Action dated Sep. 23, 2022.
U.S. Appl. No. 17/020,476, filed Sep. 14, 2020 Notice of Allowance dated Apr. 28, 2022.
U.S. Appl. No. 17/468,318, filed Sep. 7, 2021 Advisory Action dated Nov. 6, 2023.
U.S. Appl. No. 17/468,318, filed Sep. 7, 2021 Final Office Action dated Sep. 8, 2023.
U.S. Appl. No. 17/468,318, filed Sep. 7, 2021 Non-Final Office Action dated Apr. 12, 2023.
U.S. Appl. No. 17/468,318, filed Sep. 7, 2021 Notice of Allowance dated Jan. 18, 2024.
U.S. Appl. No. 17/471,015, filed Sep. 9, 2021 Advisory Action dated Feb. 2, 2024.

(56) References Cited

OTHER PUBLICATIONS

U.S. Appl. No. 17/471,015, filed Sep. 9, 2021 Final Office Action dated Oct. 12, 2023.
U.S. Appl. No. 17/471,015, filed Sep. 9, 2021 Non-Final Office Action dated Aug. 16, 2022.
U.S. Appl. No. 17/471,015, filed Sep. 9, 2021 Non-Final Office Action dated Mar. 28, 2024.
U.S. Appl. No. 17/471,015, filed Sep. 9, 2021 Non-Final Office Action dated Mar. 30, 2023.
U.S. Appl. No. 17/471,015, filed Sep. 9, 2021 Notice of Allowance dated Oct. 29, 2024.
U.S. Appl. No. 17/534,099, filed Nov. 23, 2021 Advisory Action dated Dec. 8, 2023.
U.S. Appl. No. 17/534,099, filed Nov. 23, 2021 Final Office Action dated Sep. 29, 2023.
U.S. Appl. No. 17/534,099, filed Nov. 23, 2021 Non-Final Office Action dated Mar. 14, 2024.
U.S. Appl. No. 17/534,099, filed Nov. 23, 2021 Non-Final Office Action dated Mar. 31, 2023.
U.S. Appl. No. 17/534,099, filed Nov. 23, 2021 Notice of Allowance dated Sep. 18, 2024.
U.S. Appl. No. 17/538,911, filed Nov. 30, 2021 Advisory Action dated Nov. 22, 2023.
Sonka, Momodou L., T. Campbell Arnold, and Ivan A. Kuznetsov. "Machine learning in point of care ultrasound." POCUS journal 7. Kidney (2022): 78. (Year: 2022).
U.S. Appl. No. 17/957,562, filed Sep. 30, 2022 Board Decision dated Apr. 22, 2026.
U.S. Appl. No. 17/957,562, filed Sep. 30, 2022 Notice of Allowance dated May 1, 2026.
U.S. Appl. No. 17/979,564, filed Nov. 2, 2022 Board Decision dated Mar. 4, 2026.
U.S. Appl. No. 17/987,698, filed Nov. 15, 2022 Non-Final Office Action dated Mar. 16, 2026.
U.S. Appl. No. 18/221,318, filed Jul. 12, 2023 Non-Final Office Action dated May 6, 2026.
U.S. Appl. No. 19/042,983, filed Jan. 31, 2025 Notice of Allowance dated Feb. 24, 2026.

ULTRASOUND PROBE WITH PRESSURE MEASUREMENT CAPABILITY

PRIORITY

This application is a continuation of U.S. patent application Ser. No. 17/471,015, filed Sep. 9, 2021, now U.S. Pat. No. 12,232,910, which claims the benefit of priority to U.S. Provisional Application No. 63/076,589, filed Sep. 10, 2020, each of which is incorporated by reference in its entirety into this application.

BACKGROUND

There are currently a variety of existing ultrasound systems including wired or wireless ultrasound probes that connect to displays. These systems can be used by clinicians for assessing a site such as a blood vessel for placing a vascular access device ("VAD") including a catheter. These systems can also by clinicians for assessing placement of the VAD or catheter at a chosen site. However, bodily tissue of a patient can be appreciably compressed while assessing such sites by simply using the ultrasound probes as intended. Compression of the bodily tissue can compromise vessel purchase by the VAD or catheter, which, in turn, can result in catheter extravasation that can be dangerous to the patient's health. Existing ultrasound systems do not provide for measuring bodily tissue-compressing pressure caused by the ultrasound probes during ultrasound imaging.

Disclosed herein are ultrasound probes, ultrasound systems, and ultrasound methods with pressure measurement capabilities for detecting and determining if bodily tissue is over-compressed during ultrasound imaging.

SUMMARY

Disclosed herein is an ultrasound probe including, in some embodiments, a probe body, an articulating probe head attached to the probe body, and a pressure-sensing device housed in an articulating area between the articulating probe head and the probe body.

In some embodiments, the ultrasound probe further includes a boot connecting the articulating probe head to the probe body in the articulating area. The boot is configured to cover or incorporate therein the pressure-sensing device.

In some embodiments, the pressure-sensing device is configured to detect deformations in or around an elastic material of the boot. The deformations are induced by pressing the articulating probe head into a patient.

In some embodiments, the pressure-sensing device is communicatively coupled to a controller of the ultrasound probe. The controller is configured to convert electrical signals corresponding to the deformations into measured pressure values.

In some embodiments, the ultrasound probe is configured to provide the measured pressure values to a display to be displayed to a clinician.

In some embodiments, the ultrasound probe includes logic configured to compare a measured pressure value against a threshold pressure value.

In some embodiments, the ultrasound probe includes a speaker configured to emit an audio signal to alert a clinician when the measured pressure value exceeds the threshold pressure value.

In some embodiments, the ultrasound probe includes a light-emitting diode configured to emit a visual signal to alert a clinician when the measured pressure value exceeds the threshold pressure value.

In some embodiments, the pressure-sensing device is a pressure transducer.

In some embodiments, the pressure transducer is a piezoresistive strain-gauge pressure transducer. The pressure transducer includes a strain gauge bonded to a flexible diaphragm in the articulating area between the articulating probe head and the probe body. A deformation in the diaphragm provides a corresponding measurable change in strain-gauge electrical resistance indicative of the pressure induced by pressing the articulating probe head into a patient to cause the deformation.

In some embodiments, the pressure transducer is a variable capacitance pressure transducer. The pressure transducer includes a diaphragm electrode and an opposing electrode in the articulating area between the articulating probe head and the probe body. A deformation in a flexible diaphragm affects a distance between the diaphragm electrode and the opposing electrode providing a corresponding measurable change in capacitance indicative of the pressure induced by pressing the articulating probe head into a patient to cause the deformation.

Also disclosed herein is an ultrasound system including, in some embodiments, a console and an ultrasound probe. The console includes a display configured for rendering ultrasound images on a display screen of the display. The ultrasound probe includes a probe body, an articulating probe head attached to the probe body, and a pressure-sensing device housed in an articulating area between the articulating probe head and the probe body.

In some embodiments, the ultrasound probe further includes a boot connecting the articulating probe head to the probe body in the articulating area. The boot is configured to cover or incorporate therein the pressure-sensing device.

In some embodiments, the pressure-sensing device is configured to detect deformations in or around an elastic material of the boot. The deformations are induced by pressing the articulating probe head into a patient.

In some embodiments, the pressure-sensing device is communicatively coupled to a controller of the console. The controller is configured to convert electrical signals corresponding to the deformations into measured pressure values.

In some embodiments, the ultrasound probe is configured to provide the measured pressure values to the display to be displayed to a clinician.

In some embodiments, the console includes logic configured to compare a measured pressure value against a threshold pressure value.

In some embodiments, the console includes a speaker configured to emit an audio signal to alert a clinician when the measured pressure value exceeds the threshold pressure value.

In some embodiments, the display is configured to emit a visual signal to alert a clinician when the measured pressure value exceeds the threshold pressure value.

In some embodiments, the display is configured to display visual feedback including a visualization of a target vein and a catheter placed in the target vein.

In some embodiments, the pressure-sensing device is a piezoresistive strain-gauge pressure transducer. The pressure transducer includes a strain gauge bonded to a flexible diaphragm in the articulating area between the articulating probe head and the probe body. A deformation in the diaphragm provides a corresponding measurable change in strain-gauge electrical resistance indicative of the pressure induced by pressing the articulating probe head into a patient to cause the deformation.

In some embodiments, the pressure-sensing device is a variable capacitance pressure transducer. The pressure transducer includes a diaphragm electrode and an opposing electrode in the articulating area between the articulating probe head and the probe body. A deformation in a flexible diaphragm affecting a distance between the diaphragm electrode and the opposing electrode providing a corresponding measurable change in capacitance indicative of the pressure induced by pressing the articulating probe head into a patient to cause the deformation.

Also disclosed herein is a method of an ultrasound system including, in some embodiments, an ultrasound probe-obtaining step, an ultrasound probe-placing step, an ultrasound probe-moving step, and a pressure-monitoring step. The ultrasound probe-obtaining step includes obtaining the ultrasound probe. The ultrasound probe includes a probe body, an articulating probe head attached to the probe body, and a pressure-sensing device housed in an articulating area between the articulating probe head and the probe body. The ultrasound probe-placing step includes placing the articulating probe head of the ultrasound probe on a skin surface of a patient. The ultrasound probe-moving step includes moving the articulating probe head of the ultrasound probe over the patient while ultrasound signals are emitted into the patient from the articulating probe head for ultrasound imaging. The pressure-monitoring step includes monitoring for any measured pressure values induced on the patient by the articulating probe head of the ultrasound probe in excess of a threshold pressure value.

In some embodiments, the pressure-monitoring step includes viewing the measured pressure values on a display screen of a display.

In some embodiments, the pressure-monitoring step includes monitoring for a visual signal on the display screen of the display that alerts a clinician when any measured pressure values are in excess of the threshold pressure value.

In some embodiments, the pressure-monitoring step includes monitoring for an audio signal that alerts a clinician when any measured pressure values are in excess of the threshold pressure value.

In some embodiments, the method further includes a catheter placement-adjusting step. The catheter placement-adjusting step includes adjusting catheter placement responsive to any measured pressure values in excess of the threshold pressure value to ensure a sufficient blood-vessel purchase that minimizes catheter extravasation.

These and other features of the concepts provided herein will become more apparent to those of skill in the art in view of the accompanying drawings and following description, which describe particular embodiments of such concepts in greater detail.

DESCRIPTION

Figure 2:
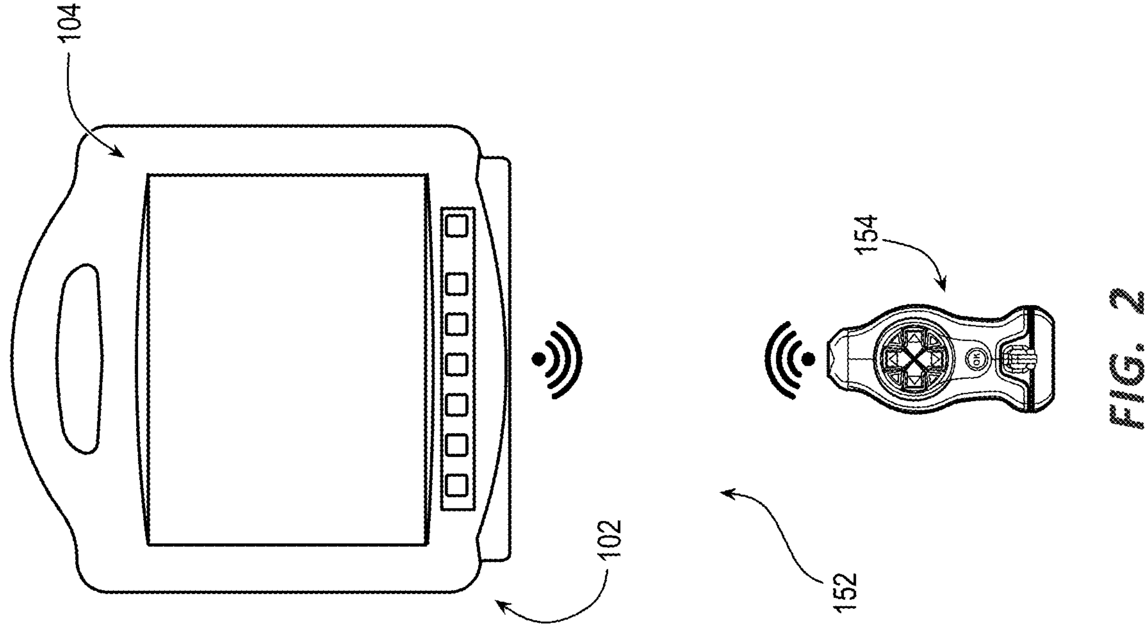
FIG. 2 illustrates a wireless ultrasound system including a console and an ultrasound probe in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Lastly, in the following description, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

Unless defined otherwise, all technical and scientific terms used herein have the same meaning as commonly understood by those of ordinary skill in the art.

As set forth above, existing ultrasound systems do not provide for measuring bodily tissue-compressing pressure caused by ultrasound probes during ultrasound imaging. Disclosed herein are ultrasound probes, ultrasound systems, and ultrasound methods with pressure measurement capabilities for detecting and determining if bodily tissue is over-compressed during ultrasound imaging.

Ultrasound Systems

Figure 1:
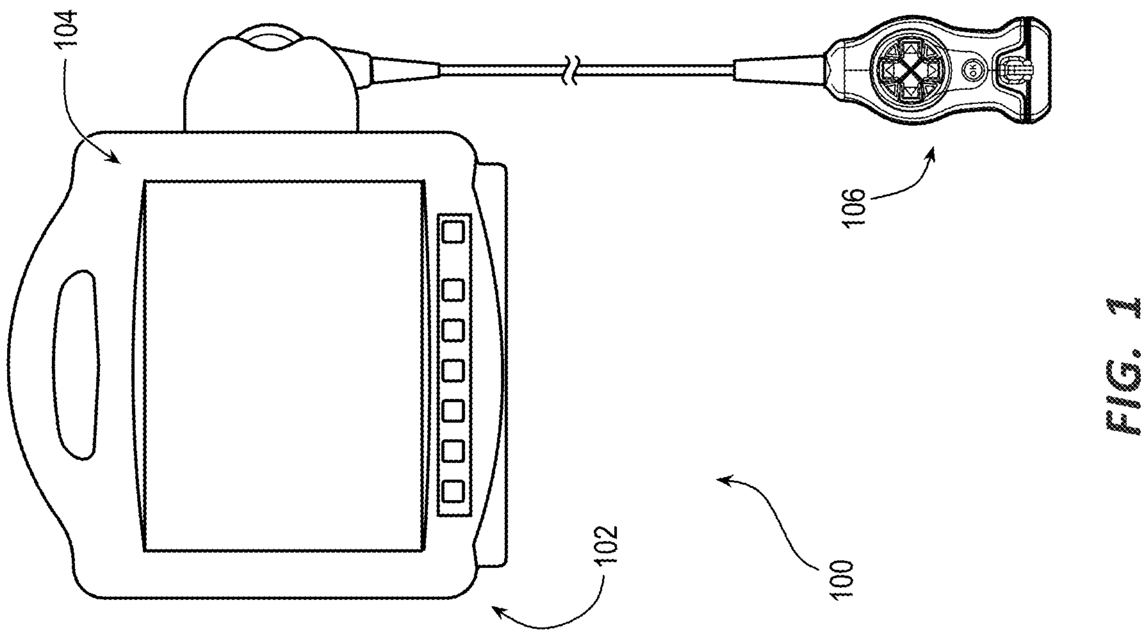
FIG. 1 illustrates a wired ultrasound system including a console and an ultrasound probe in accordance with some embodiments.
Figure 3:
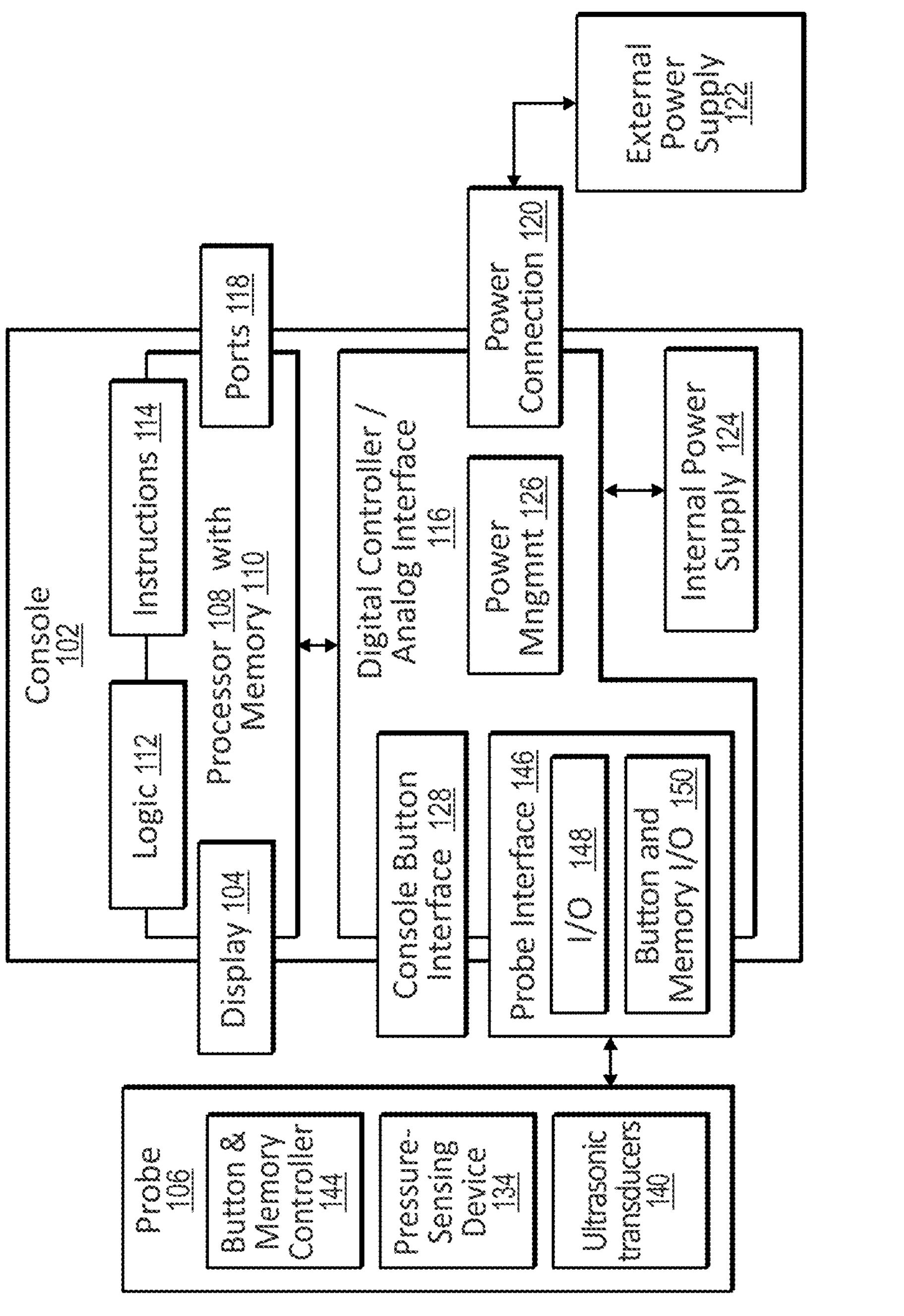
FIG. 3 illustrates a block diagram of the ultrasound system of FIG. 1 in accordance with some embodiments.

FIG. 1 illustrates a wired ultrasound system 100 in accordance with some embodiments. FIG. 3 illustrates a block diagram of the wired ultrasound system 100 in accordance with some embodiments.

As shown, the wired ultrasound system 100 includes a console 102, a display 104, and a wired ultrasound probe 106. During operation of the wired ultrasound system 100, the articulating probe head 132 of the wired ultrasound probe 106 is placed against skin of a patient. An ultrasound beam is produced so as to ultrasonically image a portion of a target such as a blood vessel beneath a surface of the skin of the patient. The ultrasonic image of the blood vessel can be depicted on the display screen of the display 104 along with the measured pressure values as set forth below. The wired ultrasound system 100 is useful for assessing access sites such as assessing a blood vessel within a body of a patient before making a percutaneous puncture with a needle to place a VAD such as a catheter into the blood vessel. The wired ultrasound system 100 is also useful for assessing access sites subsequent to placing VADs. However, it should be appreciated that the wired ultrasound system 100 can be useful in a variety of ultrasound-based medical procedures other than catheterization. For example, the percutaneous puncture with the needle can be performed to biopsy tissue of an organ of the patient.

The console 102 houses a variety of components of the wired ultrasound system 100, and it is appreciated the console 102 can take any of a variety of forms. A processor 108 and memory 110 such as random-access memory ("RAM") or non-volatile memory (e.g., electrically erasable programmable read-only memory ["EEPROM"]) is included in the console 102 for controlling various functions of the wired ultrasound system 100, as well as executing various logic operations or algorithms via logic 112 during operation of the wired ultrasound system 100 in accordance with executable instructions 114 therefor stored in the memory 110 for execution by the processor 108. For example, the console 102 is configured to instantiate by way of the instructions 114 one or more processes for controlling the functions of the wired ultrasound system 100, processing electrical signals from the ultrasonic transducers 140 of the wired ultrasound probe 106 into ultrasound images, processing electrical signals from the pressure-sensing device of the wired ultrasound probe 106 into measured pressure values, etc. A digital controller/analog interface 116 is also included with the console 102 and is in communication with both the processor 108 and other system components to govern interfacing between the wired ultrasound probe 106 and other system components set forth herein.

A controller of the console 102, optionally implemented between the processor 108 and the memory 110 of the console 102, is communicatively coupled to the pressure-sensing device 134 of the wired ultrasound probe 106 set forth below. The controller is configured to convert electrical signals corresponding to deformations of the boot 138 of the wired ultrasound probe 106 into measured pressure values, the deformations being those in or around the elastic material of the boot 138 induced by pressing the articulating probe head 132 into a patient. Notably, the logic 112 of the console 102 is configured to compare each measured pressure value against a threshold pressure value to alert a clinician when a measured pressure value exceeds the threshold pressure value. For example, the console 102 can include a speaker configured to emit an audio signal to alert the clinician when the measured pressure value exceeds the threshold pressure value. In another example, the display 104 is configured to emit a visual signal on the display screen to alert a clinician when the measured pressure value exceeds the threshold pressure value.

The wired ultrasound system 100 further includes ports 118 for connection with additional components such as optional components including a printer, storage media, a keyboard, etc. The ports 118 can be universal serial bus ("USB") ports, though other types of ports can be used for this connection or any other connections shown or described herein.

A power connection 120 is included with the console 102 to enable an operable connection to an external power supply 122. An internal power supply 124 (e.g., a battery) can also be employed either with or exclusive of the external power supply 122. Power management circuitry 126 is included with the digital controller/analog interface 116 of the console 102 to regulate power use and distribution.

The display 104 includes a display screen integrated into the console 102 to provide a graphical user interface ("GUI"), render one or more ultrasound images of the target (e.g., the blood vessel) attained by the wired ultrasound probe 106, and display 104 any related information such as the measured pressure values for the articulating probe head 132 when attaining the one-or-more ultrasound images. In addition, the display 104 can be configured to display visual feedback including a visualization of a target (e.g., a blood vessel such as a vein) and a VAD such as a catheter placed in the target. Notwithstanding the foregoing, the display 104 can alternatively be separate from the console 102 and communicatively coupled thereto. Control buttons (see FIG. 1) accessed through a console button interface 128 of the console 102 can be used to immediately call up a desired mode of the wired ultrasound system 100 to the display screen for assistance in an ultrasound-based medical procedure such as assessing the foregoing target or placing a VAD therein.

The wired ultrasound probe 106 is employed in connection with ultrasound-based visualization of a target such as a blood vessel in preparation for placing a VAD such as a catheter into the target. Such visualization gives real-time ultrasound guidance and assists in reducing complications commonly associated with VAD placement such as catheter extravasation. The wired ultrasound probe 106 is configured to provide to the console 102 electrical signals from the ultrasonic transducers 140 of the wired ultrasound probe 106, electrical signals from the pressure-sensing device of the wired ultrasound probe 106, or a combination thereof for real-time ultrasound guidance in VAD placement or other medical procedures.

FIGS. 1 and 7-11 illustrate various views of the wired ultrasound probe 106 in accordance with some embodiments.

As shown, the wired ultrasound probe 106 includes a probe body 130, an articulating probe head 132 attached to the probe body 130, and a pressure-sensing device 134 housed in an articulating area 136 between the articulating probe head 132 and the probe body 130. The wired ultrasound probe 106 further includes a boot 138 connecting the articulating probe head 132 to the probe body 130 in the articulating area 136. The boot 138 is configured to cover or incorporate therein the pressure-sensing device 134.

The articulating probe head 132 houses an array of ultrasonic transducers 140, wherein the ultrasonic transducers 140 are piezoelectric ultrasonic transducers or capacitive micromachined ultrasonic transducers ("CMUTs"). The articulating probe head 132 is configured for placement against skin of a patient proximate a prospective VAD placement site where the ultrasonic transducers 140 in the articulating probe head 132 can generate and emit the generated ultrasound signals into the patient in a number of pulses, receive reflected ultrasound signals or ultrasound echoes from the patient by way of reflection of the generated ultrasonic pulses by the body of the patient, and convert the reflected ultrasound signals into corresponding electrical signals for processing into ultrasound images by the console 102. In this way, a clinician can employ the wired ultrasound system 100 to determine a suitable VAD placement site and establish vascular access therewith.

The pressure-sensing device 134 is configured to detect deformations in or around an elastic material of the boot 138, which deformations are induced by pressing the articulating probe head 132 into a patient. The pressure-sensing device 134 can be a pressure transducer or a number of pressure transducers. For example, the pressure transducer can be a piezoresistive strain-gauge pressure transducer. Such a pressure transducer includes a strain gauge bonded to a flexible diaphragm in the articulating area 136 between the articulating probe head 132 and the probe body 130. A deformation in the diaphragm provides a corresponding measurable change in strain-gauge electrical resistance indicative of the pressure induced by pressing the articulating probe head 132 into the patient to cause the deformation. In another example, the pressure transducer is a variable capacitance pressure transducer. Such as pressure transducer includes a diaphragm electrode and an opposing electrode in the articulating area 136 between the articulating probe head 132 and the probe body 130. A deformation in a flexible diaphragm affects a distance between the diaphragm electrode and the opposing electrode providing a corresponding measurable change in capacitance indicative of the pressure induced by pressing the articulating probe head 132 into the patient to cause the deformation.

The wired ultrasound probe 106 further includes control buttons 142 for controlling certain aspects of the wired ultrasound system 100 during an ultrasound-based medical procedure, thus eliminating the need for the clinician to reach out of a sterile field around a patient to control the wired ultrasound system 100. For example, the control buttons 142 (see FIG. 7) included on the wired ultrasound probe 106 can be used to immediately call up a desired mode to the display screen by the clinician for assistance in VAD placement or some other an ultrasound-based medical procedure.

FIG. 3 shows that the wired ultrasound probe 106 further includes a button-and-memory controller 144 for governing button and ultrasound-probe operation. The button-and-memory controller 144 can include non-volatile memory (e.g., EEPROM). The button-and-memory controller 144 is in operable communication with a probe interface 146 of the console 102, which includes an input/output ("I/O") component 148 for interfacing with the ultrasonic transducers 140 and a button and memory I/O component 150 for interfacing with the button-and-memory controller 144.

Figure 5:
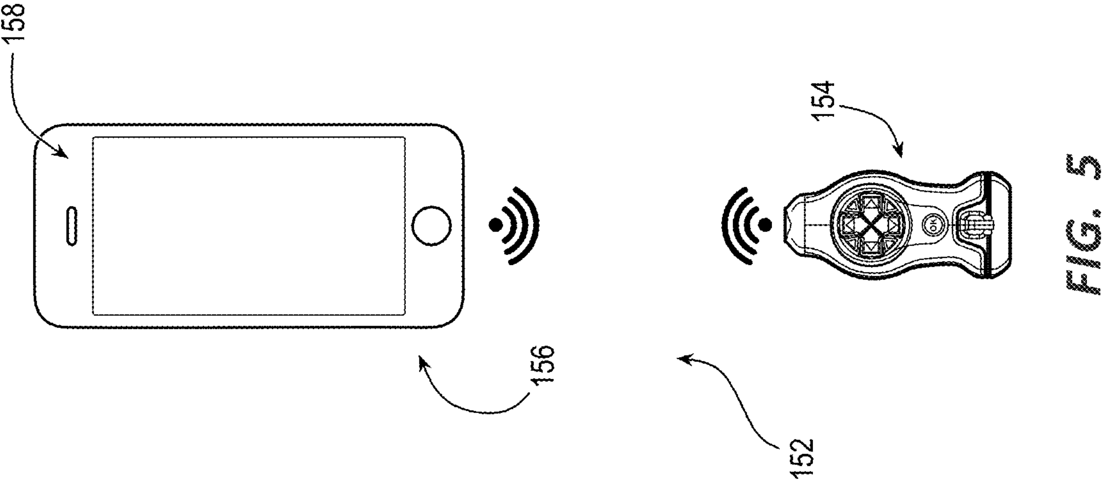
FIG. 5 illustrates a wireless ultrasound system including a companion device and an ultrasound probe in accordance with some embodiments.
Figure 4:
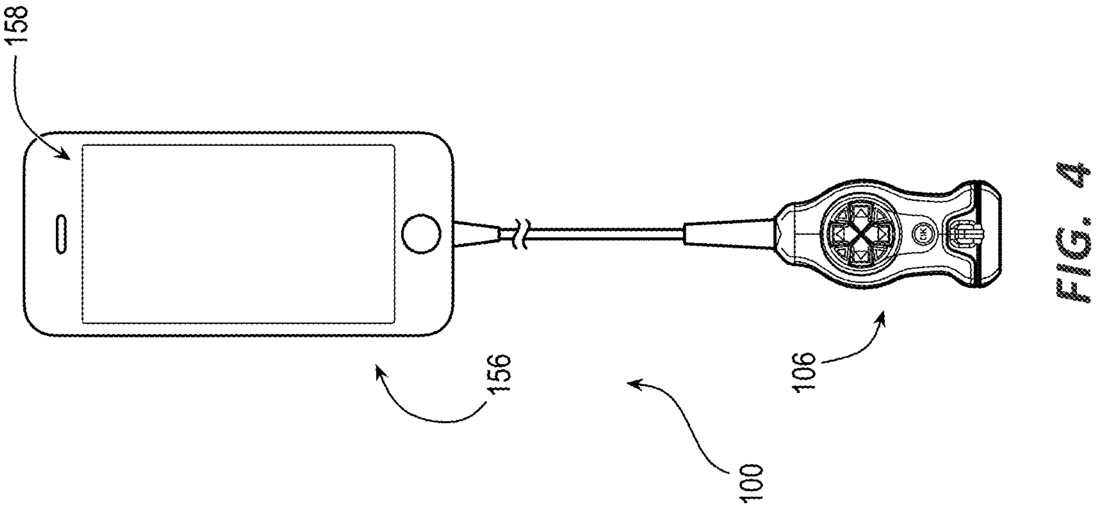
FIG. 4 illustrates a wired ultrasound system including a companion device and an ultrasound probe in accordance with some embodiments.

FIGS. 2 and 5 illustrate a wireless ultrasound system 152 in accordance with some embodiments. FIG. 4 illustrates the wired ultrasound system 100 in accordance with some other embodiments than those set forth above; indeed, the wired ultrasound probe 106 shown in FIG. 4 is like the wireless ultrasound probe 154 in that the processing of the electrical signals from the ultrasonic transducers 140 and the pressure-sensing device 134 of the wired ultrasound probe 106 is by the wired ultrasound probe 106, itself, for display on the companion device 156 through a wired connection instead of a wireless connection. FIG. 3 illustrates a block diagram of the wireless ultrasound system 152 in accordance with some embodiments.

While description of the wireless ultrasound system 152 is set forth below, it should be understood that the wireless ultrasound system 152 includes similar components to the wired ultrasound system 100 set forth above, albeit distributed differently about the wireless ultrasound system 152. For example, the wireless ultrasound probe 154, itself, can include the processor 108, the memory 110, the instructions 114, and the logic 112 of the console 102 for controlling various functions of the wireless ultrasound probe 154, converting electrical signals corresponding to deformations in or around the boot 138 of the wireless ultrasound probe 154 into measured pressure values, processing electrical signals from the ultrasonic transducers 140 into ultrasound-image data or files, and the like. Notwithstanding the foregoing, the companion device 156 (e.g., the console 102 of FIG. 2 or the smartphone, phablet, or tablet of FIGS. 4 and 5) still includes a processor, memory, instructions, logic, etc.; however, such components need not be configured for processing electrical signals from the ultrasonic transducers 140 into ultrasound-image data or files, for example. Indeed, such components can instead be configured to display ultrasound images corresponding to the ultrasound-image data or files provided by the wireless ultrasound probe 154.

As shown, the wireless ultrasound system 152 includes a wireless ultrasound probe 154 and a companion device 156 such as the smartphone, phablet, or tablet of FIGS. 4 and 5 or, in some embodiments, the console 102 of FIG. 2. The companion device 156 includes a display 158 and a wireless module 160 configured for wireless communications with the wireless ultrasound probe 154 and, optionally, a remote Electronic Health Record ("EHR") system. During operation of the wireless ultrasound system 152, the articulating probe head 132 of the wireless ultrasound probe 154 is placed against skin of a patient. An ultrasound beam is produced so as to ultrasonically image a portion of a target such as a blood vessel beneath a surface of the skin of the patient. The ultrasonic image of the blood vessel can be depicted on a display screen of the display 158 of the companion device 156 along with the measured pressure values by wirelessly providing data corresponding thereto from the wireless ultrasound probe 154 to the companion device 156. The wireless ultrasound system 152 is useful for assessing a target such as a blood vessel within a body of a patient before making a percutaneous puncture with a needle to place a VAD such as a catheter into the blood vessel. However, it should be appreciated that the wireless ultrasound system 152 can be useful in a variety of ultrasound-based medical procedures other than catheterization. For example, the percutaneous puncture with the needle can be performed to biopsy tissue of an organ of the patient.

FIGS. 7-11 illustrate various views of the wired ultrasound probe 106 in accordance with some embodiments; however, the wired ultrasound probe 106 and the wireless ultrasound probe 154 share at least the features as set forth below.

As shown, the wireless ultrasound probe 154 includes the probe body 130, the articulating probe head 132 attached to the probe body 130, and the pressure-sensing device 134 housed in the articulating area 136 between the articulating probe head 132 and the probe body 130. The wired ultrasound probe 106 further includes the boot 138 connecting the articulating probe head 132 to the probe body 130 in the articulating area 136. The boot 138 is configured to cover or incorporate therein the pressure-sensing device 134. The wireless ultrasound probe 154 with the articulating probe head 132 is capable of vein and catheter visualization. Like the wired ultrasound probe 106 set forth above, the wireless ultrasound probe 154 depicted in FIGS. 7-11 can be used for assessing access sites before and after placement of VADs.

The probe body 130 houses a printed circuit board assembly ("PCBA") 162. The PCBA 162 includes a number of electronic components of the wireless ultrasound probe 154 shown in the block diagram thereof. (See FIG. 6.) The PCBA 162 is communicatively coupled to control buttons 142 including a power button configured for toggling power to the wireless ultrasound probe 154 from power source 163 (e.g., internal battery) and various other buttons for operation of the wireless ultrasound probe 154.

Like the articulating probe head 132 of the wired ultrasound probe 106, the articulating probe head 132 of the wireless ultrasound probe 154 houses the array of ultrasonic transducers 140, wherein the ultrasonic transducers 140 are piezoelectric ultrasonic transducers or CMUTs. Again, the articulating probe head 132 is configured for placement against skin of a patient proximate a prospective VAD placement site where the ultrasonic transducers 140 in the articulating probe head 132 can generate and emit the generated ultrasound signals into the patient in a number of pulses, receive reflected ultrasound signals or ultrasound echoes from the patient by way of reflection of the generated ultrasonic pulses by the body of the patient, and convert the reflected ultrasound signals into corresponding electrical signals for processing into ultrasound images by the wireless ultrasound probe 154.

Further like the wired ultrasound probe 106, the pressure-sensing device 134 of the wireless ultrasound probe 154 is configured to detect deformations in or around the elastic material of the boot 138, which deformations are induced by pressing the articulating probe head 132 into a patient. The pressure-sensing device 134 can be a pressure transducer or a number of pressure transducers placed in the articulating area 136 between the probe body 130 and the articulating probe head 132. As set forth above, the pressure transducer can be a piezoresistive strain-gauge pressure transducer including a strain gauge bonded to a flexible diaphragm in the articulating area 136 between the articulating probe head 132 and the probe body 130. As further set forth above, the pressure transducer can be a variable capacitance pressure transducer including a diaphragm electrode and an opposing electrode in the articulating area 136 between the articulating probe head 132 and the probe body 130.

The pressure-sensing device 134 is communicatively coupled to a controller of the wireless ultrasound probe 154, which controller is optionally implemented between the processor 166 and the memory 168 of the wireless ultrasound probe 154. (See FIG. 6.) The controller is configured to convert electrical signals corresponding to the deformations in or around the elastic material of the boot 138 into the measured pressure values. The wireless ultrasound probe 154 is configured to provide the measured pressure values to the companion device 156 to be displayed to a clinician on the display screen of the companion device 156.

Notably, the wireless ultrasound probe 154 includes logic 164 configured to compare a measured pressure value against a threshold pressure value. Should the measured pressure value exceed the threshold pressure value, the wireless ultrasound probe 154 can send an electrical signal to the companion device 156 to visually or audibly alert a clinician to the foregoing measured pressure value over the threshold value. The wireless ultrasound probe 154 can additionally or alternatively include a speaker configured to emit an audio signal to alert the clinician when the measured pressure value exceeds the threshold pressure value. Additionally or alternatively, the wireless ultrasound probe 154 can include a light-emitting diode configured to emit a visual signal to alert the clinician when the measured pressure value exceeds the threshold pressure value. In this way, the wireless ultrasound probe 154 can be used to detect and determine if bodily tissue is over-compressed during ultrasound imaging. Notably, if a patient possesses excess adipose tissue, the adipose tissue can appreciably compress under the pressure induced by the articulating probe head 132. This can allow for a larger portion of, for example, a catheter to be advanced into a blood vessel. However, when the pressure induced by the articulating probe head 132 is removed, the adipose tissue can rebound causing some of the catheter to be extracted, thereby reducing the catheter purchase length. This can lead to catheter extravasation. Once the clinician is alerted of the pressure exceeding the threshold value, the clinician can check the catheter for correct placement inside the blood vessel to avoid catheter extravasation.

Figure 6:
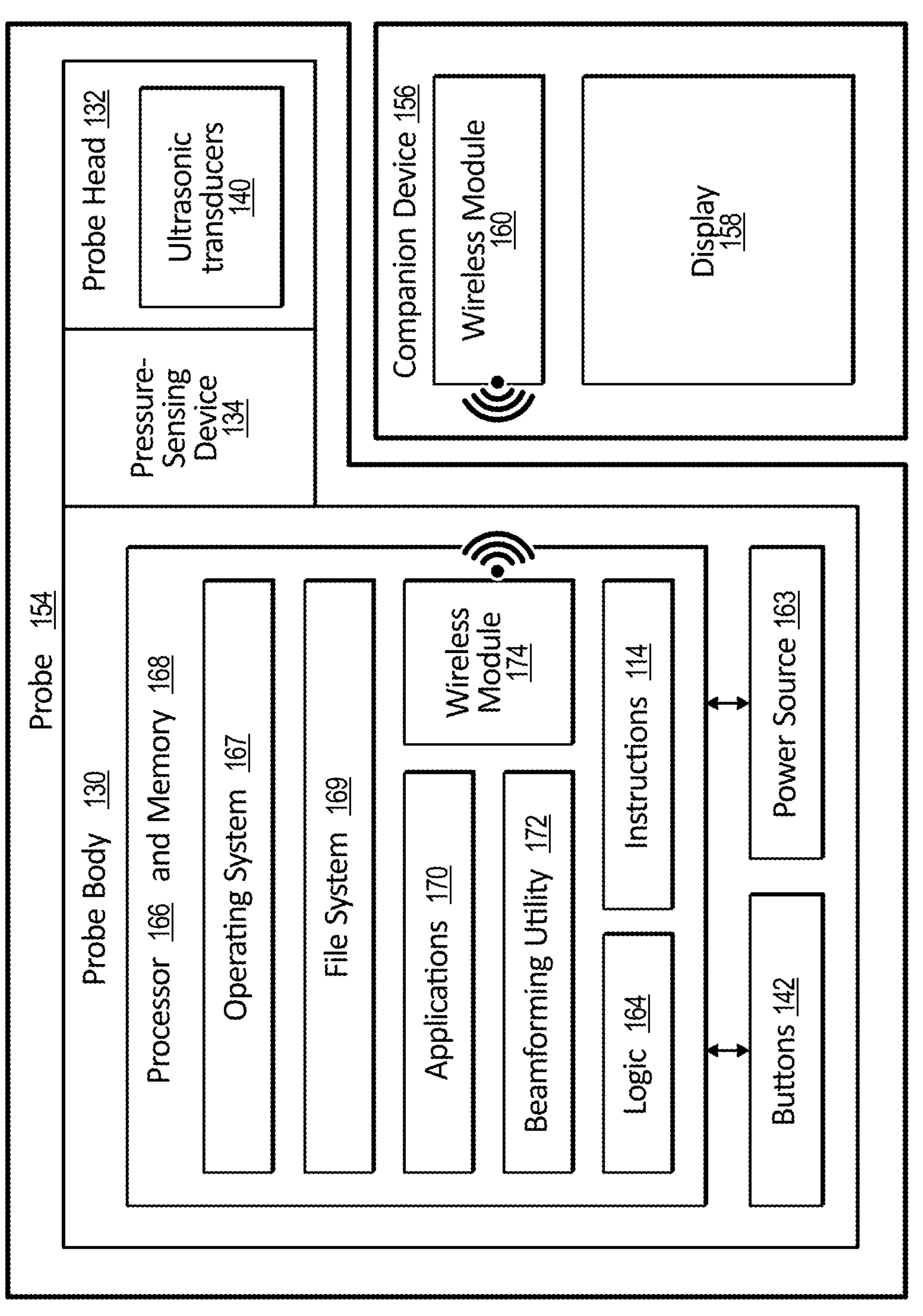
FIG. 6 illustrates a block diagram of the ultrasound system of FIG. 2, FIG. 4, or 5 in accordance with some embodiments.
Figure 7:
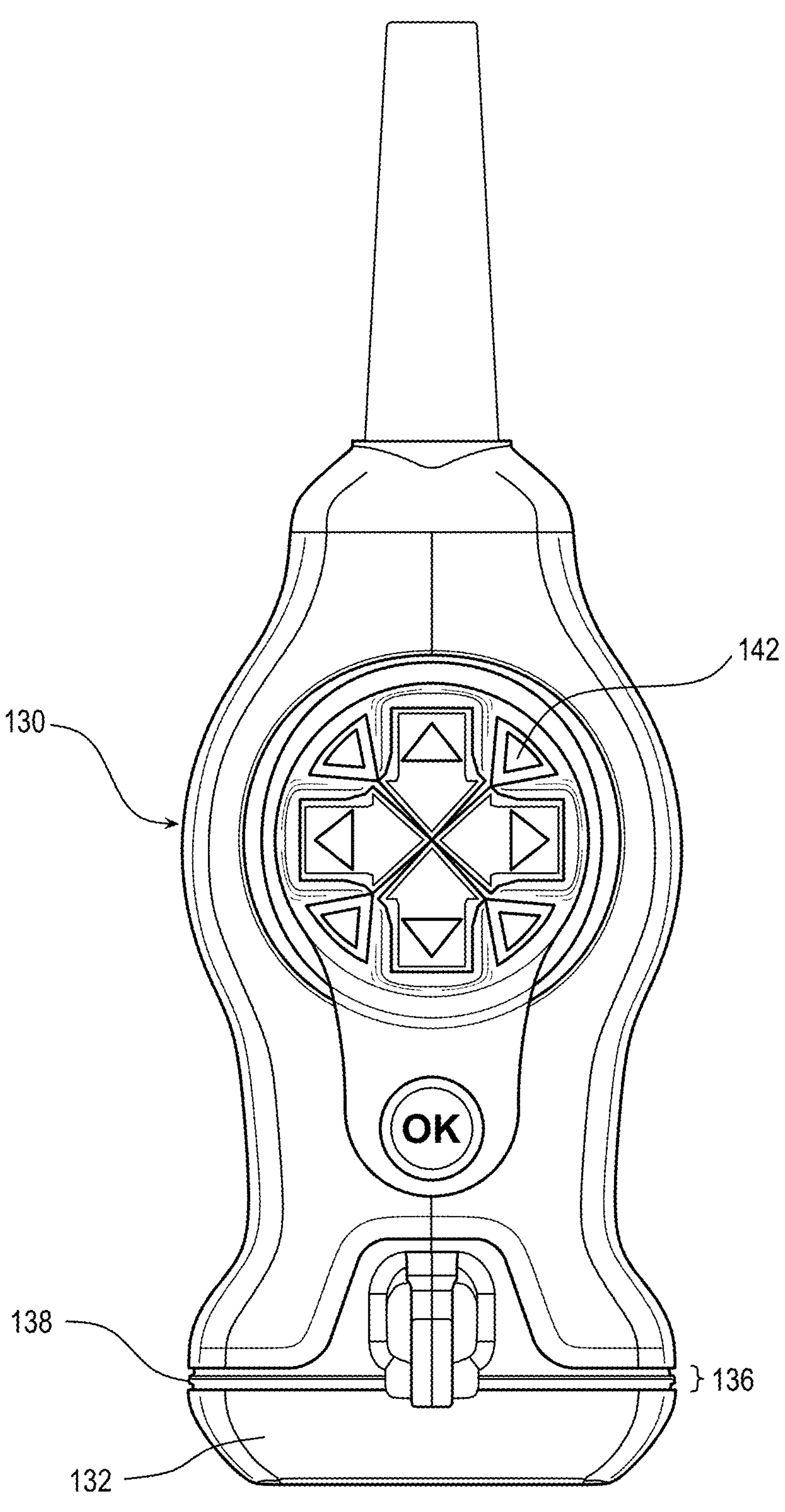
FIG. 7 illustrates a front view of an ultrasound probe including a pressure-sensing device in accordance with some embodiments.
Figure 8:
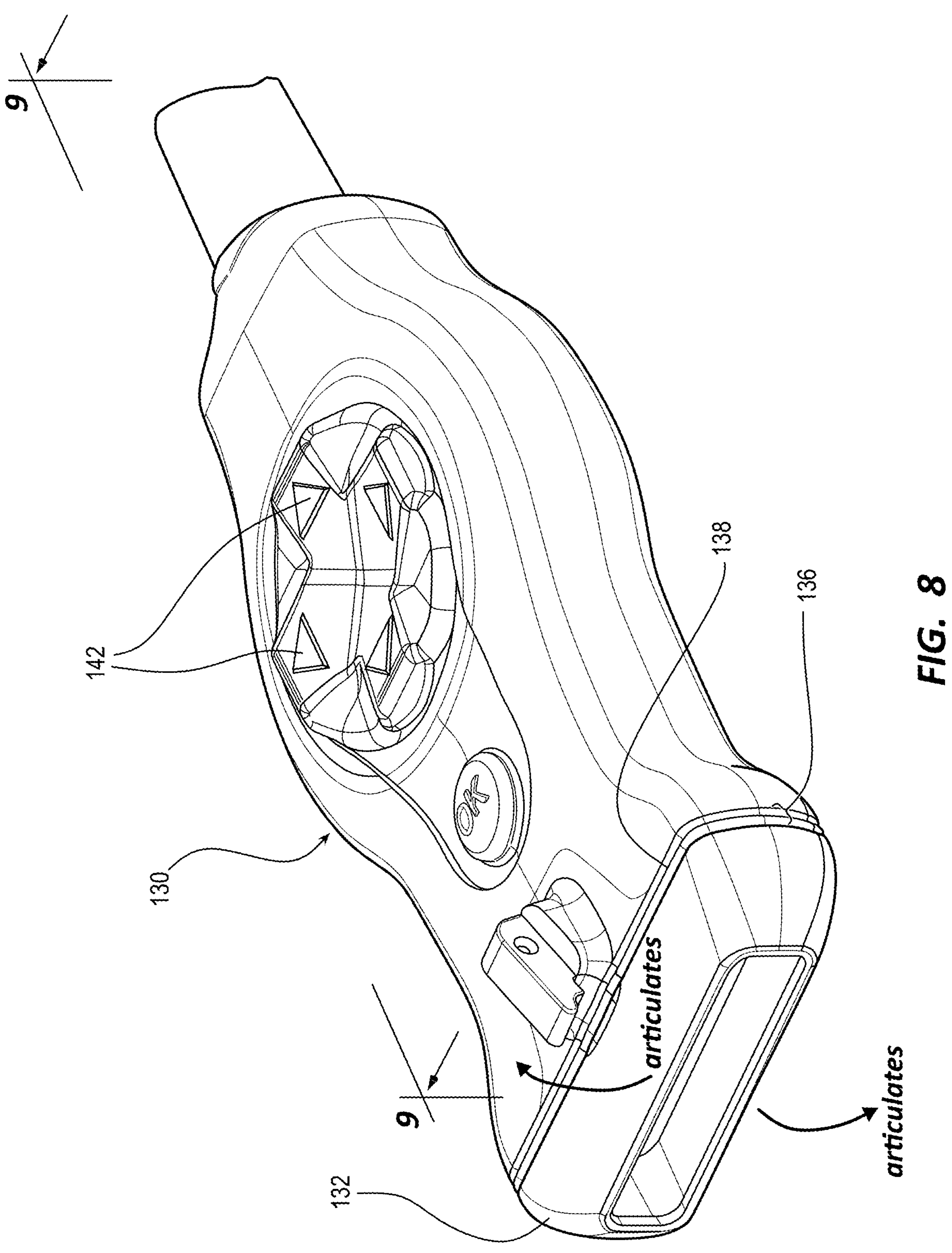
FIG. 8 illustrates a perspective view of the ultrasound probe in accordance with some embodiments.
Figure 9:
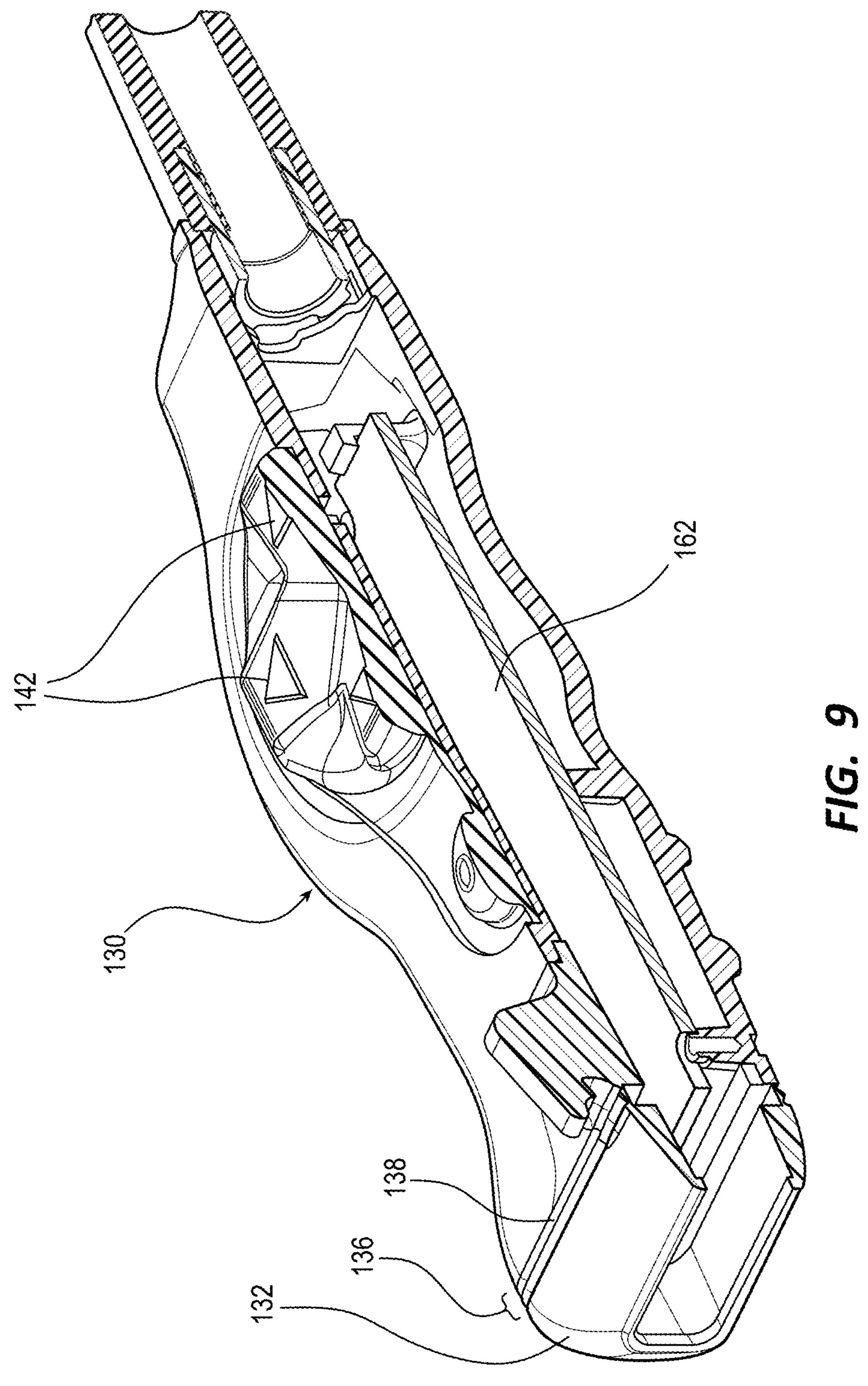
FIG. 9 illustrates a cross section of the ultrasound probe in accordance with some embodiments.
Figure 10:
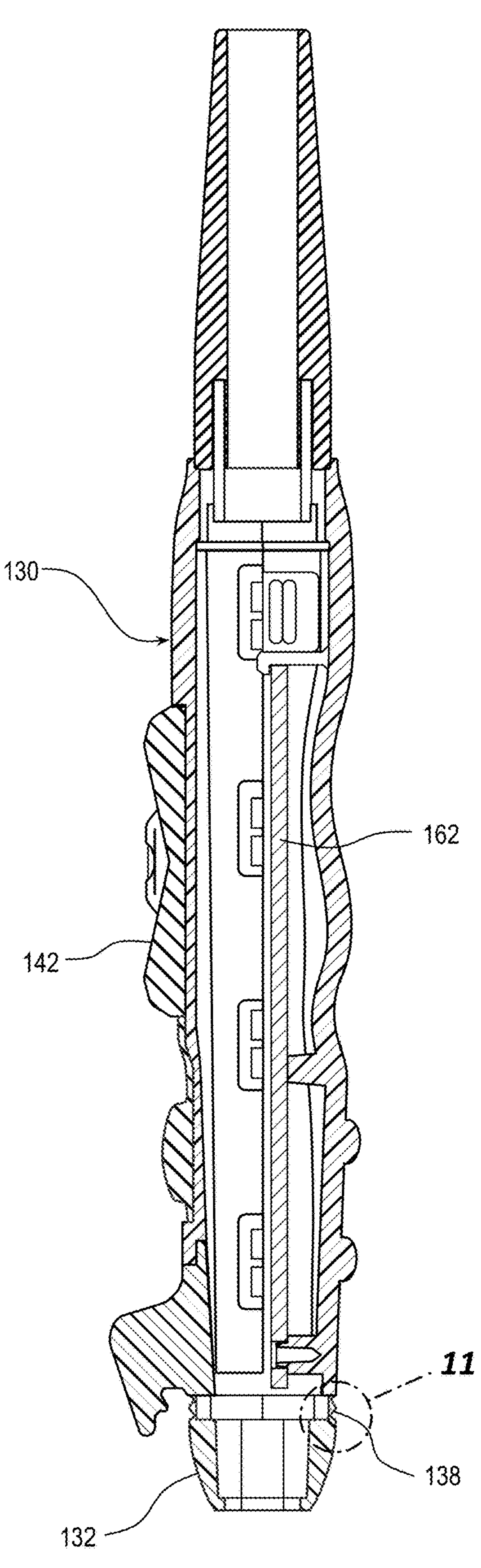
FIG. 10 illustrates another cross section of the ultrasound probe in accordance with some embodiments.
Figure 11:
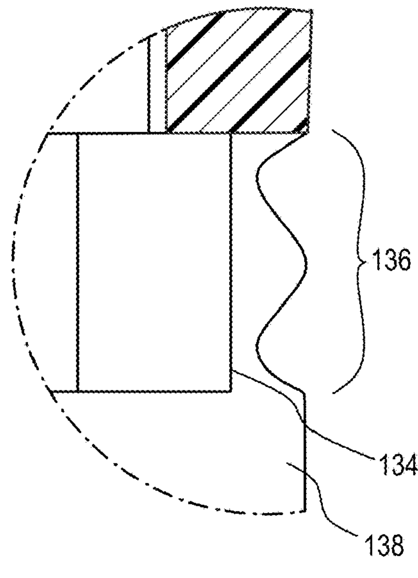
FIG. 11 illustrates a detailed view of an articulating area of the ultrasound probe including the pressure-sensing device in accordance with some embodiments.

FIG. 6 illustrates a block diagram of the wireless ultrasound system 152 in accordance with some embodiments.

As shown, the wireless ultrasound probe 154 includes a processor 166 for governing system functionality by employment of a general-purpose operating system 167, memory 168 including a file system 169, and applications 170 that can be stored in the memory 168 and executed by the processor 166. Some of the applications 170 can provide a user interface to allow a clinician to monitor the pressure induced on a patient by the articulating probe head 132. A beamforming utility 172, including suitable circuitry is also controlled by the processor 166 to enable signals to be produced, received, and further processed. For example, the beamforming utility 172 produces electrical signals received by the ultrasonic transducers 140 in the articulating probe head 132. The articulating probe head 132 passes ultrasound signals corresponding to the electrical signals into an area of a patient and receives reflected ultrasound signals from the patient. The reflected ultrasound signals, in turn, are converted into corresponding electrical signals by the ultrasonic transducers 140 in the articulating probe head 132, which electrical signals are provided to the beamforming utility 172 for further processing into ultrasound-image data or files for display on the companion device 156. Note that the wireless ultrasound probe 154 can include different components such as more or fewer components than those set forth herein, including those components such as the wireless module 174 that enable the wireless ultrasound probe 154 to operate in a wireless manner with the companion device 156.

The wired or wireless ultrasound system 100 or 152 with the integrated pressure-sensing device 134 provides versatility beyond vein visualization for VAD placement as set forth above. Having a wired or wireless ultrasound system 100 or 152 that not only provides for ultrasound imaging but ensures that the application of the wired or wireless ultrasound probe 106 or 154 against a patient's skin does not result in excessive pressure induced by the articulating probe head 132, advantageously reduces a risk of catheter extravasation.

Methods

Methods include a method of using the wired or wireless ultrasound system 100 or 152. For example, the method includes one or more steps selected from an ultrasound probe-obtaining step, an ultrasound probe-placing step, an ultrasound probe-moving step, a pressure-monitoring step, and a catheter placement-adjusting step.

The ultrasound probe-obtaining step includes obtaining the wired or wireless ultrasound probe 106 or 154. As set forth above, the wired and wireless ultrasound probes 106 and 154 include the probe body 130, the articulating probe head 132 attached to the probe body 130, and the pressure-sensing device 134 housed in the articulating area 136 between the articulating probe head 132 and the probe body 130.

The ultrasound probe-placing step includes placing the articulating probe head 132 of the wired or wireless ultrasound probe 106 or 154 on a skin surface of a patient.

The ultrasound probe-moving step includes moving the articulating probe head 132 of the wired or wireless ultrasound probe 106 or 154 over the patient while ultrasound signals are emitted into the patient from the articulating probe head 132 for ultrasound imaging.

The pressure-monitoring step includes monitoring for any measured pressure values induced on the patient by the articulating probe head 132 of the ultrasound probe in excess of a threshold pressure value. The monitoring can include viewing the measured pressure values on the display screen of the display 104 of the console 102 or the display 158 of the companion device 156. Such monitoring can also include monitoring for an audio signal or a visual signal on the display screen of the display 104 or 158. Such signals alert a clinician when any measured pressure values are in excess of the threshold pressure value.

The method further includes a catheter placement-adjusting step. The catheter placement-adjusting step includes adjusting catheter placement responsive to any measured pressure values in excess of the threshold pressure value to ensure a sufficient blood-vessel purchase by the catheter that minimizes catheter extravasation.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures can be made from the particular embodiments disclosed herein without departing from the scope of the concepts provided herein.

What is claimed is:

1. An ultrasound imaging method, comprising:

grasping an ultrasound probe, the ultrasound probe comprising:

an articulating probe head attached to a probe body; and a pressure-sensing device housed in an articulating area between the articulating probe head and the probe body;

placing the articulating probe head of the ultrasound probe on a skin surface of a patient;

moving the articulating probe head of the ultrasound probe over the skin surface of the patient while ultrasound signals are emitted into the patient from the articulating probe head; and monitoring for measured pressure values induced on the patient by the articulating probe head of the ultrasound probe to determine whether a threshold pressure value has been exceeded.

2. The ultrasound imaging method according to claim 1, further comprising viewing the measured pressure values on a display communicating with the ultrasound probe.

3. The ultrasound imaging method according to claim 2, wherein monitoring for measured pressure values includes monitoring for a visual signal on the display that indicates the threshold pressure value has been exceeded.

4. The ultrasound imaging method according to claim 1, wherein the ultrasound probe includes a speaker, and wherein monitoring for measured pressure values includes listening for an audio signal that indicates the threshold pressure value has been exceeded.

5. The ultrasound imaging method according to claim 1, wherein the ultrasound probe includes a light-emitting diode, and wherein monitoring for measured pressure values includes looking for a visual signal from the light-emitting diode that indicates the threshold pressure value has been exceeded.

6. The ultrasound imaging method according to claim 1, wherein the ultrasound probe further comprises a boot connecting the articulating probe head to the probe body in the articulating area to cover or incorporate therein the pressure-sensing device, further comprising detecting deformations in or around an elastic material of the boot induced by the articulating probe head.

7. The ultrasound imaging method according to claim 6, wherein the pressure-sensing device is communicatively coupled to a controller of the ultrasound probe, further comprising converting electrical signals corresponding to the deformations into measured pressure values by the pressure-sensing device and communicating the electrical signals to the controller.

8. The ultrasound imaging method according to claim 1, wherein the pressure-sensing device is a piezoresistive strain-gauge pressure transducer including a strain gauge bonded to a flexible diaphragm in the articulating area between the articulating probe head and the probe body, wherein a deformation in the flexible diaphragm provides a corresponding measurable change in strain-gauge electrical resistance, and wherein monitoring for measured pressure values comprises monitoring for the corresponding measurable change in strain-gauge electrical resistance.

9. The ultrasound imaging method according to claim 1, wherein the pressure-sensing device is a variable capacitance pressure transducer including a diaphragm electrode and an opposing electrode in the articulating area between the articulating probe head and the probe body, wherein a deformation in a flexible diaphragm affecting a distance between the diaphragm electrode and the opposing electrode provides a corresponding measurable change in capacitance, and wherein monitoring for measured pressure values comprises monitoring for the corresponding measurable change in the capacitance.

* * * * *